United States Patent
Govreen-Segal et al.

(10) Patent No.: US 10,933,165 B2
(45) Date of Patent: Mar. 2, 2021

(54) COMPOSITE IMPLANT MATERIAL

(71) Applicant: G & G BIOTECHNOLOGY LTD., Haifa (IL)

(72) Inventors: Dael Govreen-Segal, Hod Hasharon (IL); Haim Dvir, Nesher (IL); Jacky Govrin-Yehudain, Caesarea (IL)

(73) Assignee: G & G BIOTECHNOLOGY LTD, Haifa (IL)

( * ) Notice: Subject to any disclaimer, the term of this patent is extended or adjusted under 35 U.S.C. 154(b) by 0 days.

(21) Appl. No.: 15/701,883

(22) Filed: Sep. 12, 2017

(65) Prior Publication Data

US 2018/0000991 A1    Jan. 4, 2018

Related U.S. Application Data

(63) Continuation-in-part of application No. PCT/IL2016/050277, filed on Mar. 13, 2016.
(Continued)

(51) Int. Cl.
*A61F 2/12* (2006.01)
*A61L 27/50* (2006.01)
(Continued)

(52) U.S. Cl.
CPC .............. *A61L 27/50* (2013.01); *A61F 2/12* (2013.01); *A61L 27/18* (2013.01); *A61B 6/502* (2013.01);
(Continued)

(58) Field of Classification Search
CPC ............... A61F 2/12; A61F 2210/0076; A61F 2210/0057; A61F 2250/0091;
(Continued)

(56) References Cited

U.S. PATENT DOCUMENTS

| | | | |
|---|---|---|---|
| 2,676,892 A | 4/1954 | McLaughlin | |
| 2,797,201 A | 6/1957 | Veatch | |

(Continued)

FOREIGN PATENT DOCUMENTS

| | | |
|---|---|---|
| CN | 1303716 A | 7/2001 |
| CN | 2457979 Y | 11/2001 |

(Continued)

OTHER PUBLICATIONS

"Bondurant, Stuart, et al. Silicone implants and breast imaging. 1999. Retrived from URL: http://www.ncbi.nlm.nih.gov/books/NBK44781/Jan. 1, 1999 (Jan. 1, 1999) chapter 12", 308 pages.
(Continued)

*Primary Examiner* — Brian A Dukert
*Assistant Examiner* — Rebecca Lynee Zimmerman
(74) *Attorney, Agent, or Firm* — Graeser Associates International Inc.; D'vorah Graeser

(57) ABSTRACT

A prosthetic implant with improved properties, suitable for implantation to the human body, comprising a composite comprising a base material and a plurality of additives, wherein the additives are selected from radiolucent additives and/or hyperechoic additives; or wherein the additives are selected to reduce the solvent concentration by between 5%-95%; or wherein the additives are selected to increase the elastic modulus by more than 20%; or wherein the additives are selected for combining these effects.

21 Claims, 14 Drawing Sheets

Related U.S. Application Data

(60) Provisional application No. 62/132,071, filed on Mar. 12, 2015, provisional application No. 62/132,078, filed on Mar. 12, 2015, provisional application No. 62/153,608, filed on Apr. 28, 2015.

(51) Int. Cl.
*A61L 27/18* (2006.01)
*A61B 6/00* (2006.01)

(52) U.S. Cl.
CPC .......... *A61F 2210/0057* (2013.01); *A61F 2210/0076* (2013.01); *A61F 2250/0091* (2013.01); *A61L 2430/04* (2013.01)

(58) Field of Classification Search
CPC ..... A61F 2250/0098; A61F 2250/0036; A61L 27/40; A61L 27/50; A61L 27/18; A61L 2430/04; A61B 6/502
See application file for complete search history.

(56) References Cited

U.S. PATENT DOCUMENTS

| | | | |
|---|---|---|---|
| 3,030,215 A | 4/1962 | Veatch | |
| 3,189,662 A | 6/1965 | Vaughn, Jr. | |
| 3,230,184 A | 1/1966 | Alford | |
| 3,247,158 A | 4/1966 | Alford | |
| 3,308,491 A | 3/1967 | Spence | |
| 3,548,420 A | 12/1970 | Spence | |
| 3,622,437 A | 11/1971 | Hobaica | |
| 3,681,787 A | 8/1972 | Perras | |
| 3,683,424 A | 8/1972 | Pangman | |
| 3,811,133 A | 5/1974 | Harris | |
| 3,986,213 A | 10/1976 | Lynch | |
| 4,019,209 A | 4/1977 | Spence | |
| 4,021,589 A | 5/1977 | Copley | |
| 4,072,635 A | 2/1978 | Jeram | |
| 4,298,998 A | 11/1981 | Naficy | |
| 4,380,569 A | 4/1983 | Shaw | |
| 4,459,145 A | 7/1984 | Elsholz | |
| 4,470,160 A | 9/1984 | Cavon | |
| 4,650,889 A | 3/1987 | Plueddemann | |
| 4,676,795 A | 6/1987 | Grundei | |
| 4,681,587 A | 7/1987 | Eberl | |
| 4,773,909 A | 9/1988 | Chaglassian | |
| 4,795,464 A | 1/1989 | Eberl | |
| 4,849,456 A | 7/1989 | Champion | |
| 4,861,804 A | 8/1989 | Nakanishi | |
| 4,992,312 A | 2/1991 | Frisch | |
| 5,011,494 A | 4/1991 | Von | |
| 5,055,497 A | 10/1991 | Okada | |
| 5,081,997 A | 1/1992 | Bosley, Jr. | |
| 5,147,398 A | 9/1992 | Lynn | |
| 5,171,269 A | 12/1992 | Bark | |
| 5,202,362 A | 4/1993 | Hermele | |
| 5,236,454 A | 8/1993 | Miller | |
| 5,246,454 A | 9/1993 | Peterson | |
| 5,258,578 A | 11/1993 | Smith | |
| 5,358,521 A | 10/1994 | Shane | |
| 5,407,445 A | 4/1995 | Tautvydas | |
| 5,480,430 A | 1/1996 | Carlisle | |
| 5,496,367 A | 3/1996 | Fisher | |
| 5,522,896 A * | 6/1996 | Prescott | A61B 17/0057 623/23.56 |
| 5,534,023 A | 7/1996 | Henley | |
| 5,545,217 A | 8/1996 | Offray | |
| 5,549,671 A | 8/1996 | Waybright | |
| 5,590,430 A | 1/1997 | Sereboff | |
| 5,653,755 A | 8/1997 | Ledergerber | |
| 5,658,330 A | 8/1997 | Carlisle | |
| 5,723,006 A | 3/1998 | Ledergerber | |
| 5,741,877 A | 4/1998 | Tiffany | |
| 5,779,734 A | 7/1998 | Ledergerber | |
| 5,871,497 A | 2/1999 | Young | |
| 5,902,335 A | 5/1999 | Snyder | |
| 6,146,418 A | 11/2000 | Berman | |
| 6,183,514 B1 | 2/2001 | Becker | |
| 6,187,043 B1 | 2/2001 | Ledergerber | |
| 6,194,476 B1 | 2/2001 | De | |
| 6,271,278 B1 | 8/2001 | Park | |
| 6,296,800 B1 | 10/2001 | Stelter | |
| 6,387,981 B1 | 5/2002 | Zhang | |
| 6,464,726 B1 | 10/2002 | Heljenek | |
| 6,478,656 B1 | 11/2002 | Khouri | |
| 6,486,237 B1 | 11/2002 | Howe | |
| 6,544,287 B1 | 4/2003 | Johnson | |
| 6,733,893 B2 | 5/2004 | Suzuki | |
| 6,835,763 B2 | 12/2004 | Ellis | |
| 6,932,840 B1 | 8/2005 | Bretz | |
| 6,967,221 B2 | 11/2005 | Meguriya | |
| 6,972,313 B2 | 12/2005 | Howe | |
| 7,988,731 B2 | 8/2011 | Govrin-Yehudian | |
| 9,339,371 B2 | 5/2016 | Dvir | |
| 9,775,703 B2 | 10/2017 | Govreen-Segal | |
| 2002/0038147 A1 | 3/2002 | Miller | |
| 2002/0103539 A1 | 8/2002 | Stelter | |
| 2002/0193878 A1 | 12/2002 | Bowman | |
| 2003/0047718 A1 | 3/2003 | Narayan | |
| 2003/0074084 A1 | 4/2003 | Nakao | |
| 2003/0144411 A1 | 7/2003 | Howe | |
| 2003/0153244 A1 | 8/2003 | Chen | |
| 2004/0049269 A1 | 3/2004 | Corbitt | |
| 2004/0073305 A1 | 4/2004 | Schneider-Nieskens | |
| 2004/0153151 A1 | 8/2004 | Gonzales | |
| 2005/0052414 A1 | 3/2005 | Park | |
| 2005/0197698 A1 | 9/2005 | Schneider-Nieskens | |
| 2005/0252414 A1 | 11/2005 | Craig | |
| 2006/0025859 A1 | 2/2006 | Stelter | |
| 2006/0136056 A1 | 6/2006 | Wohl | |
| 2006/0161266 A1 | 7/2006 | Schwibner | |
| 2006/0224239 A1 | 10/2006 | Tiahrt | |
| 2007/0050026 A1 | 3/2007 | Carvallo | |
| 2007/0050027 A1 | 3/2007 | McGhan | |
| 2007/0135916 A1 | 6/2007 | Maxwell | |
| 2007/0293945 A1 | 12/2007 | Snyder | |
| 2008/0203263 A1 | 8/2008 | Carnevali | |
| 2009/0299472 A1 | 12/2009 | Huang | |
| 2009/0299473 A1 | 12/2009 | Govrin-Yehudian | |
| 2011/0060411 A1 | 3/2011 | Govrin-Yehudian | |
| 2012/0277860 A1 * | 11/2012 | Dvir | A61F 2/12 623/11.11 |
| 2015/0305853 A1 * | 10/2015 | Schuessler | A61F 2/12 623/8 |
| 2018/0036116 A1 | 2/2018 | Govreen Segal | |

FOREIGN PATENT DOCUMENTS

| | | |
|---|---|---|
| CN | 103068413 A | 4/2013 |
| CN | 203107780 U | 8/2013 |
| EP | 0821575 A1 | 2/1998 |
| EP | 0874604 A1 | 11/1998 |
| EP | 1432562 A1 | 6/2004 |
| EP | 1663072 A2 | 6/2006 |
| EP | 2962662 | 1/2016 |
| JP | 2002296940 A | 10/2002 |
| RU | 2197509 C1 | 1/2003 |
| RU | 2233644 | 8/2004 |
| RU | 2233644 C1 | 8/2004 |
| WO | 9632908 A1 | 10/1996 |
| WO | 9719654 A1 | 6/1997 |
| WO | 9726025 A1 | 7/1997 |
| WO | 03026866 A1 | 4/2003 |
| WO | 2005020843 A2 | 3/2005 |
| WO | 2005086067 | 9/2005 |
| WO | 2006069677 A2 | 7/2006 |
| WO | 2006114786 A2 | 11/2006 |
| WO | 2006133366 A1 | 12/2006 |
| WO | 2009018105 | 2/2009 |
| WO | 2011086537 | 7/2011 |
| WO | 2011086537 A2 | 7/2011 |

(56) References Cited

FOREIGN PATENT DOCUMENTS

| WO | 2013015987 | | 1/2013 |
|---|---|---|---|
| WO | 2013070290 | A1 | 5/2013 |

OTHER PUBLICATIONS

Bondurant, Stuart et al., "Silicone implants and breast imaging.", (19990000), pp. 264-284, URL: http://www.ncbi.nlm.nih.gov/books/NBK44781, (Jan. 1, 1999) 559 pages.
Brazilian Office Action for BR1120120175360 dated Oct. 8, 2018, 13 pages.
Chinese Office Action dated Oct. 9, 2018 issued in CN Patent Application No. 201680015309.5, dated Oct. 9, 2018, 3 pages.
Chinese Office Action for Application No. 201680015309.5, dated Jun. 21, 2019, 10 pages.
Columbian Office Action issued in CO Application No. NC2017/0010151, dated Feb. 2, 2019, 9 pages.
Combined Search Report and Written Opinion for parent PCT Application No. PCT/182011/050217, dated Jul. 5, 2011 (14 pages).
Guarding against potential inhibitors /poisons of platinum catalyzed addition cure release coatings' published by Dow-Corning as part of their 'Facts on File Series', published in 2003 (3 pages).
Ishida, Hatsuo. "Controlled interphases in glass fiber and particulate reinforced polymers: Structure of silane coupling agents in solutions and on substrates." The interfacial interactions in polymeric composites. Springer Netherlands, 1993. 169-199. 31 pages.
JP2002296940—English-translation (17 pages).
Moyer, Hunter R. M.D.; Ghazi, Bahair H. M.D.; Losken, Albert M.D. "The Effect of Silicone Gel Bleed on Capsular Contracture: A Generational Study" Plastic and Reconstructive Surgery: Oct. 2012—vol. 130—Issue 4—p. 793-800.
Notice of Allowance dated May 9, 2018 for U.S. Appl. No. 15/249,352 (pp. 1-7).
Notice of Allowance dated Oct. 17, 2018 for U.S. Appl. No. 15/686,457 (pp. 1-10).
Office Action dated Jul. 13, 2018 for U.S. Appl. No. 15/686,457 (pp. 1-6).
Office Action dated Nov. 1, 2017 for U.S. Appl. No. 15/249,352; (pp. 1-9).
Office Action for corresponding Chinese Application No. 201190000276.X, dated Nov. 7, 2012, provided with translation. (4 pages).
Office action for corresponding EP application 06728299.6, Issued Sep. 1, 2011 (4 pages).
Office action for corresponding EP application 06728299.6, dated Jan. 20, 2011 (3 pages).
PEEK Biomaterials in Trauma, Orthopedic, and Spinal Implants. Biomaterials. 2007;28(32):4845-4869.
Russian Office Action for Application No. 2017132258, dated Aug. 23, 2019, 11 pages.
Russian Search Report for Application No. 2017132258, dated Aug. 15, 2019, 3 pages.
Search report for corresponding EP application 06728299.6, dated Feb. 22, 2010. (9 pages).
Search report for related PCT/IL06/00501 dated Jan. 9, 2008 (7 pages).
Japanese Office Action (with English language translation) for Application No. JP2017-566230, dated Feb. 10, 2020, 7 pages.
Brazilian Office Action for App. No. BR1120170194317, dated Jun. 9, 2020, 4 pages.
Russian Office Action for Application No. 2017132258, dated Jan. 13, 2020, 5 pages.
Office Action (including English translation) for App. No. IL254462, dated Aug. 30, 2020, 5 pages.
English language Japanese Office Action for App. No. JP2017-566230, dated Sep. 8, 2020, 5 pages.
Office Action for App. No. IL254462, dated Aug. 30, 2020, 3 pages.

\* cited by examiner

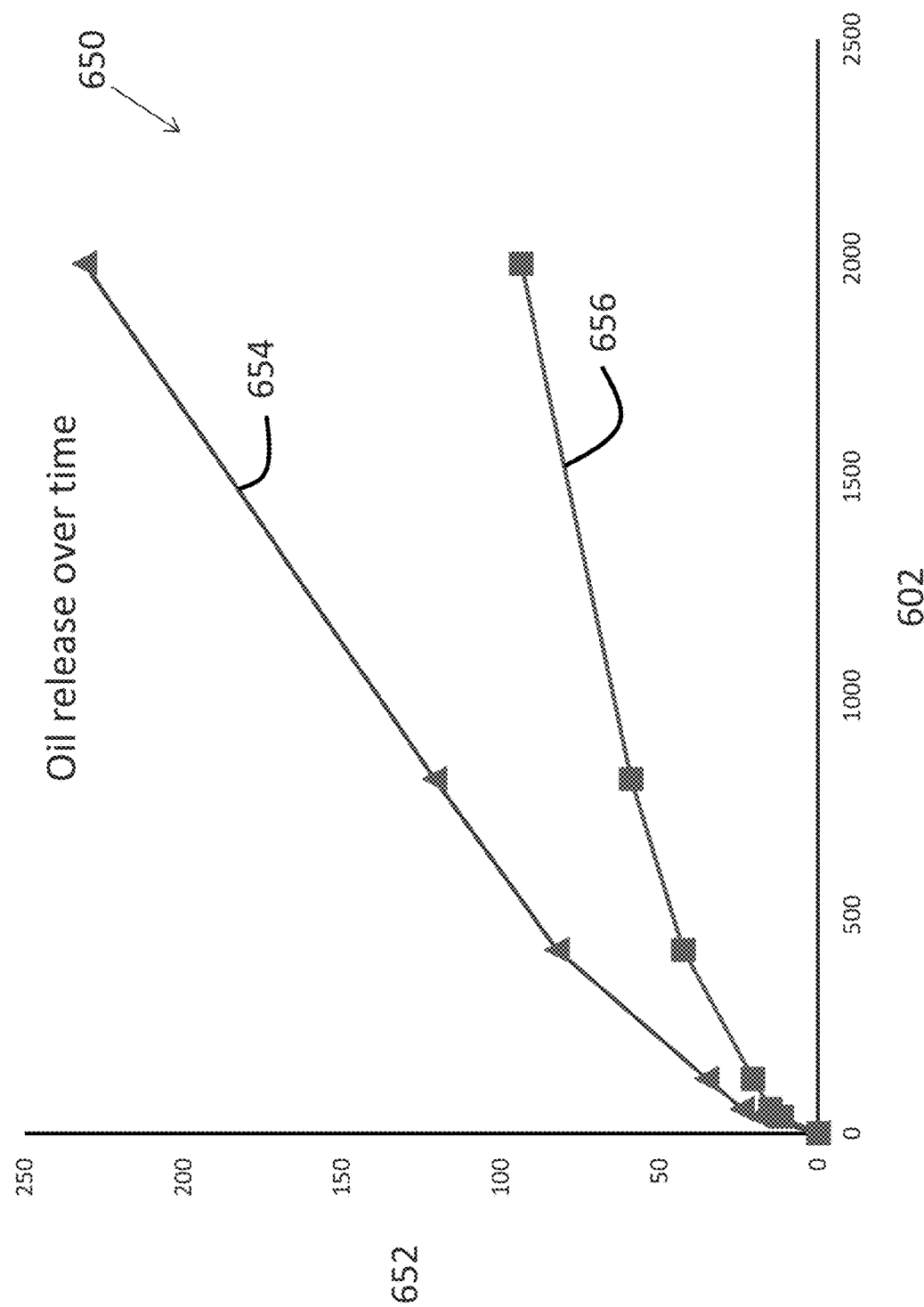

COMPOSITE IMPLANT MATERIAL

FIELD OF THE INVENTION

The present invention relates generally to implantable prosthetic devices and specifically to implantable prosthetic devices featuring a composite of a base material and an additive material.

BACKGROUND OF THE INVENTION

In the last century reconstructive and cosmetic surgery has become a common practice. Specifically reconstructive breast surgery has been developed to allow reconstruction of a woman's breast that was affected by procedures such as mastectomy. Cosmetic breast surgery has also become available to amend the appearance of a woman's breast, for example by adding an implant to increase the size of the breast, to correct asymmetries, change shape and fix deformities.

The material chosen for the implant must have the appropriate resilience, elasticity and pliability, which provides it with a specific feeling when being sensed. Generally it is desirable to provide an implant which provides a specific shape and mimics the feel of real human tissue at the position of the implant. It is important that the implant maintain its form and feel for extended periods, to prevent the need for additional surgery.

Prior art implants used today for breast implant surgery for example comprise an outer shell typically formed from vulcanized silicone rubber (elastomer) which can be single or multi layered, smooth or textured, with or without barrier layer/s, or covered with polyurethane foam; and an inner content typically composed of silicone gel or saline. There are also double lumen implants that are combinations of both silicone and saline such as the Becker implant from Mentor Corp.

Prior art implants present challenges in several areas which are described in more detail below including: imaging, such as mammograms; gel bleed from the implant; and mechanical and chemical issues.

Imaging studies are carried out on the augmented breast for two primary reasons: 1) To evaluate the breast tissues (e.g. for lesions); 2) To evaluate the breast implants for complications—for example it is important to be able to clearly identify the integrity of the implant's shell. When evaluating breast tissues it is desirable that the implants do not obscure the tissues under examination or interfere with the chosen imaging technique. Further, it is desirable to be able to clearly identify the integrity of the implant's shell.

Three main imaging modalities are used in breast examination:
  Ultrasonography;
  Mammography (X-Ray); and
  MRI (Magnetic resonance imaging).

Silicone gel as used in standard implants is radiopaque. Therefore, in mammography the typical representation of an implant will be white with no further details of the tissue in front of or behind the implant. This is illustrated in FIG. 3A which is a mammogram of a breast with a prior art implant. As shown in the mammogram 300, the implant 302 appears completely white (opaque to x-ray) showing no detail of the tissue in front of it or behind it. Breast tissue 304 not obscured by the implant is visible in the mammogram 300.

The problem is further illustrated in FIGS. 3C and 3D which are x-ray images of excised breast tissue following a lumpectomy from a patient in which microcalcifications were identified. The lines such as line 334 in the images are guide wires for spatial marking of the tumor sites to aid the surgeons who performed the excision. In image 330 which is an x-ray of only the excised tissue 336, circles 332 indicate the microcalcifications. In image 340 of FIG. 3D the same x-ray machine and method have been used with a prior art implant 342 placed above the excised tissue 336. As shown in FIG. 3D, the excised tissue 336 is almost completely obscured by the prior art implant 342 where the outline of tissue 336 is faintly visible but no details are visible. Therefore diagnosis of potentially life-threatening diseases is hampered by the prior art implants which are radiopaque.

Accordingly, in order to overcome the known limitation of implant opacity, women with implants typically have 4 extra x-ray images (2 on each breast), as well as the 4 standard images taken during a screening mammogram. The mammograms for women with breast implants are thus performed in the normal fashion as for a breast without implants and then again in an oblique position with the implant pushed back as much as possible out of the frame of the mammogram (known as the Eklund implant displacement technique). Implant displacement mammograms have several disadvantages:

The implant is pushed back against the chest wall and the breast is pulled forward over it. This theoretically allows better imaging of the front part of each breast but typically, 30% of breast tissue can still be obscured by the implant;
  It is a complex technique that requires significant sensitivity and skill by mammographers. Thus the facility and the mammographer need to have experience on imaging of women with breast implants;
  They can only be performed as long as the implant remains soft and free of encapsulation. They can be uncomfortable in women who have had hard scar tissue form around the implants (capsular contractures);
  The patient is exposed to double the amounts of radiation of a normal mammography.
  Examination of the augmented breasts is more time consuming;
  Patients exhibit extensive anxiety about implant damage from the compression process.

FIG. 8A is a flow diagram illustrating the steps required for performing a mammogram on a patient with an implant. The process begins at stage 1 with the implant surgery. After a period of time at stages 2-4 the patient undergoes a routine screening mammography which herein refers to a periodic screening mammography not related to specific symptoms. In stage 2 standard mediolateral oblique 45 degree and craniocaudal mammography images are taken for each breast. In stage 3 since the implant is radiopaque it is necessary to perform implant displacement followed by mediolateral oblique 45 degree and craniocaudal imaging for each breast. In some cases stage 4 will be required where the patient exhibits rigid encapsulation and mediolateral 90 degree imaging will be performed for each breast. Finally, in stage 5 the mammography images can be evaluated to detect anomalies not obscured by the implants.

When used with ultrasonography, silicone gel is anechoic. Since the silicone gel has a density similar to liquid, the speed of sound in the implant is slightly slower but similar to that of water (and the surrounding tissues) and therefore ultrasonography will usually detect an echo or reverberation of the shell with additional reverberation artifacts from the gel itself. Reverberations from the gel create visual noise on the picture which interferes with the ability of the radiologist to detect abnormalities.

Soft tissues have a conduction speed of 1540 m/sec. Water, which has a conduction speed of 1492 m/sec will appear as dark and the more echoic the material, the more white the image will appear. Silicone has a conduction speed of approximately 997 m/sec and the slowing of the sound waves in the implant is what causes many of the reverberations and artifacts seen.

This is illustrated in FIGS. 5A and 5C which are ultrasound images of the edges of prior art breast implants in situ. As shown in FIG. 5A, the shell 502 of a prior art implant is visible in an ultrasound image 500 captured with a 12 MHz probe.

The top of image 500 is the interface of the probe with the skin. Then there is a representation of tissue 502 comprising skin, fat, glands and other tissue, followed by the shell of the silicone implant 504. The gel 508 is seen as the black area. Reverberations seen as visual noise 506 caused by the implant are also visible in image 500 in the area which should be black (the gel 508). This noise is seen extending 1.5 cm into the area of the image 500. The noise also extends above the shell creating a cloud like snow over the tissue area 502 of the image which is intended for diagnosis. Similarly, FIG. 5C shows an ultrasound image 520 captured with a 17 MHz probe where both the implant shell 522 and the visual noise caused by the implant 524 are visible.

When there is a rupture in the implant, the extravasated gel may migrate to other areas in the body. However, due to its anechoic nature and high resemblance to water, free silicone gel can often be mistaken for a pathology such as a cyst. This is illustrated in FIG. 5E which shows an ultrasound image 540 of tissue with silicone gel present. The silicone is indicated by circle 542 and as shown, it appears as a bubble and may be interpreted as a cyst or other tissue by the radiographer.

The background art therefore does not teach or suggest a prosthetic implant material that does not obscure the tissues under examination or interfere with the chosen imaging technique. Further, as shown, prior art implants cause visual noise that interferes with the ability of the radiologist to detect abnormalities. Finally it would be preferable, in case of a rupture of the shell, for the silicone material to remain cohesive and prevent migration to other parts of the body or for the silicone material to be easily identifiable so as to be able to differentiate it from tissue.

A further problem with prior art implants is gel bleed from an intact implant. Gel bleed is a common term describing a diffusion based phenomena where the solvent (silicone oil) as a part of silicone gel diffuses/bleeds through the shell. Diffusion is a phenomenon where a substance flows from a region of high concentration to a region of low concentration due to chemical potential. The diffusive flux is negatively proportional to the concentration gradient and the coefficient of proportionality is the diffusion coefficient. The flux goes from regions of high concentration to regions of low concentration. Reducing the concentration gradient would therefore reduce the gel bleed.

It is undesirable to have silicone bleed into bodily tissues as the free silicone can elicit a foreign body response resulting in granulomas and calcifications in the breast which can be misinterpreted in radiological screenings as breast tissue abnormalities. Free silicone can also easily migrate into the lymphatic system and accumulate in the lymph nodes (usually in the axilla) resulting in lumps and lymphadenopathy. Gel bleed has also been tagged as one of the causes for capsular contracture. Research in animal models has concluded that "There is a dose-dependent relationship between silicone gel bleed and capsule compliance that is independent of the cohesivity of the silicone" (Moyer HR1, Ghazi B H, Losken A. Plast Reconstr Surg. 2012 October; 130(4):793-800).

Efforts to reduce gel bleed have focused on two directions:

Adding and improving the barrier layer/s in the shells;
Changing the composition of the solvent to reduce the amount of low molecular silicone moieties that may easily diffuse through the elastomeric shell and replacing them with higher molecular weight silicone moieties.

While these efforts have resulted in 4th and 5th generation breast implants which have somewhat reduced gel bleed, they have not solved the problem completely. Furthermore, these solutions are only somewhat effective while the implant shell is intact. When the implant shell is compromised due to rupture or degradation, these solutions provide significantly reduced effectiveness allowing elevated rates of solvent migration into the body. It would therefore be desirable to enhance the implants to reduce solvent bleed from intact as well as ruptured implants.

Finally, it has been show in recent years that it is desirable to use more cohesive gels for several reasons:

Imitate more closely the surrounding breast tissue for a breast that feels more natural;
To reduce gel bleed as described above;
To improve the dynamic mechanical interface with the breast by serving as a scaffold to support the shape of the augmented breast;
To prevent flow and dispersion of gel in the body in the case of rupture or shell degradation;
Prevent breakage of the gel during insertion or use in the body;
To better maintain the form of the implant during normal use. This is especially important in shaped or anatomical implants; and
To prevent or reduce wrinkling. Often implants suffer from visible folds and wrinkles (especially in women with thin tissue coverage).

Current silicone gels come in varying degrees of cohesiveness. Silicone gel cohesion can be increased by increasing the degree of crosslinking resulting in a mesh of higher crosslinking density. The average distance between two adjacent crosslinks is thus reduced.

Thus increased crosslinking has advantages, however, excessive increases in crosslinking may result in the gel breaking even without externally applied forces because of internal residual stresses. For example, when taking a gel such as NUSIL Med 3-6300, the mixing ratio specified is 3:1 part A to part B. Part A contains the catalyst and part B contains the crosslinker and therefore changing the mixing ration results in different crosslinking densities and different cohesions. However, increasing the crosslinker component excessively results in the gel breaking. In this case, mixing at a ratio of 3:2 results in a highly cohesive gel that breaks and fractures without any applied load.

Therefore, for the reasons stated above, a more cohesive gel is desired but simply increasing the crosslinking causes the gel to fracture and therefore another mechanism to make the gel more cohesive is required.

SUMMARY OF THE INVENTION

The present invention overcomes the deficiencies of the background art by providing a prosthetic implant comprising a composite implant material further comprising a base material and additives. The term base material as used herein refers to a polymer network further comprising a free molecule which may be either a solvent or free polymer chain. The free molecule therefore defines whether the polymer network has a gel or elastomer form. The composite material of the presently described invention may herein be alternatively referred to as implant material, composite implant material, or composite material. The addition of additives to the base material provides several improvements:

The implant material has improved radiology characteristics such as improved radiolucency and decreased associated visual noise in ultrasound images. Further, the composite material is uniquely identifiable using imaging modalities and can be easily differentiated from tissue or other materials;

The phenomena of gel bleed can be generalized to include bleed of free molecules from a base material. The implant material reduces the total amount of free molecules resulting in the reduction of the concentration gradient and therefore reduction in free molecule bleed. As described above, the concentration gradient is the driving force for free molecule bleed and therefore reducing the free molecule concentration reduces free molecule bleed.

Further, the additives incorporated in the base material limit free molecule bleed based on two additional mechanisms. The first mechanism is physical, where at some point as the composite material shrinks because of the loss of free molecule in the base material, the additives constrain further shrinkage because of their physical size and their contact with each other. The second mechanism is based on the large cumulative surface area of the additives. The free molecule in the base material wets the additive surface due to surface interactions and does not tend to be removed (unless there is drying, desorption or replacement with another liquid that has higher affinity to the surface). By contrast, prior art implants are not constrained and can theoretically lose a high percentage of their solvent to diffusion;

The additives in the implant material increase the cross-linking density/cohesion of the base material, thus strengthening (reinforcing) the base material while maintaining its integrity. The implant material with a reinforced base material provides several advantages when used in a breast implant:

More closely imitates the surrounding breast tissue for a breast that feels more natural;

The reinforced implant presents a desirable smooth contour because of the cohesive form-stable nature;

Prevents or reduces wrinkling;

Reduces solvent bleed from an intact implant;

Maintains the form and shape of the implant over time;

Prevents breakage during implantation or use;

Improves the dynamic mechanical interface with the breast by serving as a scaffold to support the shape of the augmented breast;

Prevents the flow and dispersion of base material in the body in the case of rupture or shell degradation, and reduces free solvent that can be absorbed by the body in such cases.

The additives are added to the base material as a volume substitution element creating a two phased system with a continuous phase and a dispersed phase or bi-continuous system. As an example, 30% of the implant's base material volume can be replaced by the additives. Optionally, the additives comprise less than 1% by volume of the composite material. Optionally, the additives comprise more than 1% by volume of the composite material. Optionally, the additives comprise up to 60% by volume of the composite material. Optionally, the additives comprise up to 90% by volume of the composite material.

The implant material is suitable for use in an encapsulated implant according to at least some embodiments of the present invention, in which the implant features a shell and the implant material, such that the implant material is contained within the shell.

Further, the present invention conforms to the requirements of an implantable prosthesis such as being able to provide a specific three-dimensional shape and maintain the shape for many years, preferably for the lifetime of the patient in which the implant is installed; having a specific feel, preferably imitating the feel of human or animal tissue, such as the feel of a real breast; being bio-durable such that it is not ruined by interaction with the human or animal body; being bio-compatible so that the patient's health is not detrimentally affected by the implant even under extreme circumstances: for example the filler (base material with additives) is required to be non-toxic in case of leakage from the implant.

According to preferred embodiments of the present invention, the implant is adapted for use as a breast implant.

According to at least some embodiments of the present invention, the implant material comprises a base material, such as for example silicone gel, and a lower density material. Silicone gel density is ~1 gr/cm$^3$ in the order of densities of other liquids, such as water and organic solvents. The lower density material therefore has a density lower than ~1 gr/cm$^3$. Optionally and preferably, the lower density material comprises a gas.

In an exemplary embodiment of the invention, the implant may be provided in various sizes, for example extending from 50 cc to 1500 cc or larger or smaller. Optionally, the implant may be implanted in other areas of the body other than the breast, for example to replace or augment testicles, pectorals, a chin, cheeks, a calf, buttocks or other parts of the human or an animal body, while exhibiting tactile properties similar to natural tissue.

According to a preferred embodiment of the present invention a prosthetic implant, suitable for implantation to the human body comprises a composite material comprising a base material and a plurality of additives, wherein the additives are selected from radiolucent additives and/or hyperechoic additives. Preferably the additives are selected from the group consisting of: additives comprising at least one of glass, ceramic, metal, polymers, PMMA, polyacrylonitrile, polybutadiene, PEEK, natural rubber, synthetic rubber, amorphous polymer or semi-crystalline polymer; additives between 1 nm and 1 mm in diameter; additives comprising a three-dimensional shape comprising spherical, fibrous, platelet, flakes, amorphous, crystalline, semi-sphere, rod, disk or combinations of these shapes or irregular versions of these shapes; hollow additives; porous additives; solid additives; additives comprising at least 2 materials; additives with surface roughness of between 0.2 nm and 40 nm RRMS; additives comprising a gas; additives comprising a non-solvent liquid; additives comprising a non-silicone gel; additives formed as a micro-lumen; and a combination of the above.

Optionally, different additives may be combined together to benefit from their combined properties for example but not limited to use of additives that are hyper-echoic combined with additives that serve for reinforcement of the material. Optionally additives may be independent within the base or combined in a physical structure, for example but not limited to additives connected as chains or a mesh to also benefit from the physical scaffolding property.

Optionally, additives may be rigid or compressible.

Optionally, additives may be dispersed throughout the material homogenously or optionally may be limited to certain areas for example but not limited to near the shell. Optionally additives may be dispersed with varying densities throughout the implant material, optionally with continuous changes in density or abrupt differences in density.

Optionally the base material comprises a silicone gel. Optionally, the implant comprises a plurality of shells, including at least one inner shell and at least one outer shell; wherein the at least one inner shell is at least partially surrounded by the outer shell; wherein the outer shell is filled with the base material and a plurality of hyperechoic additives, and wherein the inner shell is filled with the base material and a plurality of radiolucent additives.

According to another preferred embodiment of the present invention a composite material suitable for implantation to the human body, comprises a base material and a plurality of additives, wherein the additives are selected from radiolucent additives and/or hyperechoic additives. Preferably the additives comprise up to 60% by volume of the composite material. Preferably, the additives comprise up to 90% by volume of the composite material. Optionally, the base material is silicone gel.

According to another preferred embodiment of the present invention a prosthetic implant, suitable for implantation to the human body, comprises a composite material comprising a base material and a plurality of additives, wherein the additives are selected such that the solvent concentration of the composite material is between 5%-95% of the solvent concentration of the base material.

Optionally the additives reduce the solvent concentration of the base material by 20% to 80%. Optionally the additives reduce the solvent concentration of the base material by 40% to 60%. Optionally the additives reduce the solvent concentration of the base material by up to 50%.

Preferably the additives are selected from the group consisting of: additives comprising at least one of glass, ceramic, metal, polymers, PMMA, polyacrylonitrile, polybutadiene, PEEK, natural rubber, synthetic rubber, amorphous polymer or semi-crystalline polymer; additives between 1 nm and 1 mm in diameter; additives comprising a three-dimensional shape comprising spherical, fibrous, platelet, flakes, amorphous, crystalline, semi-sphere, rod, disk or combinations of these shapes or irregular versions of these shapes; hollow additives; porous additives; solid additives; additives comprising at least 2 materials; additives with surface roughness of between 0.2 nm and 40 nm RRMS; additives comprising a gas; additives comprising a non-solvent liquid; additives comprising a non-silicone gel; additives formed as a micro-lumen; and a combination of the above.

Optionally the base material comprises a silicone gel. Optionally, the implant comprises a plurality of shells, including at least one inner shell and at least one outer shell; wherein the at least one inner shell is at least partially surrounded by the outer shell; wherein the outer shell is filled with the base material and a higher concentration of additives closer to the outer shell, and wherein the inner shell is filled with the base material and an increasing concentration of additives relative to the distance from the inner shell.

According to another preferred embodiment of the present invention a composite material suitable for implantation to the human body, comprises a base material and a plurality of additives, wherein the additives are selected such that the solvent concentration of the composite material is 5%-95% of the solvent concentration of the base material. Preferably the additives comprise up to 60% by volume of the composite material. Preferably, the additives comprise up to 90% by volume of the composite material. Optionally, the base material is silicone gel.

According to another preferred embodiment of the present invention a prosthetic implant, suitable for implantation to the human body, comprises a composite material comprising a base material and a plurality of reinforcing additives, wherein the additives are selected such that the elastic modulus of the composite material is greater than the elastic modulus of the base material by at least 20%. Preferably, the elastic modulus is between 100% and 1000% greater. Preferably the elastic modulus is between 100% and 500% greater.

Preferably, the additives are chosen such that the cohesiveness of the composite material increases as measured by a penetration test the result of which is 5%-99.5% shorter than that of the base material, wherein the penetration is measured after 5 seconds using a Lab-Line (Melrose, Ill., USA) penetrometer with a 12 gram shaft and a foot of 1 inch diameter.

Preferably the additives are selected from the group consisting of: additives comprising at least one of glass, ceramic, metal, polymers, PMMA, polyacrylonitrile, polybutadiene, PEEK, natural rubber, synthetic rubber, silicone, amorphous polymer or semi-crystalline polymer; additives between 1 nm and 1 mm in diameter; additives comprising a three-dimensional shape comprising spherical, fibrous, platelet, flakes, amorphous, crystalline, semi-sphere, rod, disk or combinations of these shapes or irregular versions of these shapes; hollow additives; porous additives; solid additives; additives comprising at least 2 materials; additives with surface roughness of between 0.2 nm and 40 nm RRMS; additives comprising a gas; additives comprising a non-solvent liquid; additives comprising a non-silicone gel; additives formed as a micro-lumen; and a combination of the above. Optionally, the base material is silicone gel.

Optionally, the implant comprises a plurality of shells, including at least one inner shell and at least one outer shell; wherein the at least one inner shell is at least partially surrounded by the outer shell; wherein the outer shell is filled with the base material and a low concentration of additives, and wherein the inner shell is filled with the base material and a high concentration of additives.

According to another preferred embodiment of the present invention a composite material suitable for implantation to the human body, comprises a base material and a plurality of additives, wherein the additives are selected such that the elastic modulus at 1 Hz of the composite material is 20%-5000% greater than the elastic modulus of the base material. Preferably, the additives are chosen such that the cohesiveness of the composite material increases as measured by a penetration test the result of which is 5%-99.5% shorter than that of the base material, wherein the penetration is measured after 5 seconds using a Lab-Line (Melrose, Ill., USA) penetrometer with a 12 gram shaft and a foot of 1 inch diameter.

According to another preferred embodiment of the present invention a method for performing a screening mammography of a breast comprising an implant, comprises: performing a mammography on one or both breasts; and evaluating the mammographic images; wherein implant displacement is not performed during the performing of the mammography, wherein the implant comprises a composite material comprising a base material and a plurality of additives, wherein the additives are selected from radiolucent additives.

According to another preferred embodiment of the present invention a method for performing a mammography of a breast comprising an implant, comprises: performing a mammography on one or both breasts; wherein the resulting mammographic image comprises the implant and wherein the implant comprises a composite material comprising a base material and a plurality of additives, wherein the additives are selected from radiolucent additives such that the implant does not obscure breast tissue in the image.

According to another preferred embodiment of the present invention a method for detection in a patient of extravasated implant material that has escaped from a ruptured implant, comprises: implanting an implant comprising a composite material comprising a base material and a plurality of additives, wherein the additives are selected from hyperechoic or hypoechoic additives; performing ultrasonography on the patient; and detecting the extravasated material by its hyperechoic or hypoechoic signature or response.

According to another preferred embodiment of the present invention a method for diagnosis of cancerous tissue in a breast comprising an implant, comprises: implanting a prosthetic implant, suitable for implantation to the human body, comprising a composite material comprising a base material and a plurality of additives, wherein the additives are selected from radiolucent additives and/or hyperechoic additives; capturing a diagnostic radiology image of the breast wherein the image comprises the prosthetic implant; and determining the presence of calcifications in breast tissue visible on the image behind or in front of the implant.

Preferably the additives comprise up to 60% by volume of the composite material. Preferably, the additives comprise up to 90% by volume of the composite material. Optionally, the base material is silicone gel.

Optionally, the implant of any of the above embodiments comprises a plurality of shells, including at least one inner shell and at least one outer shell; wherein the at least one inner shell is at least partially surrounded by the outer shell; wherein the outer shell is filled with the base material and a first concentration of additives, and wherein the inner shell is filled with the base material and a second concentration of additives. Preferably the first concentration is lower than the second concentration. Alternatively the first concentration is higher than the second concentration.

Optionally, the implant comprises multiple areas or compartments. Optionally, the implant material is only present in selected areas or compartments of the implant. Optionally, the implant comprises different concentrations of base material and/or additives in different areas. Optionally, a single additive is used or alternatively multiple additives are used. Optionally, different concentrations of base material are provided with different combinations of additives in different areas of the implant.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 6A and 6B are photographs and a graph showing comparative diffusion of a prior art implant gel and the composite material of the presently claimed invention;

DESCRIPTION OF THE PREFERRED EMBODIMENTS

Figure 1:
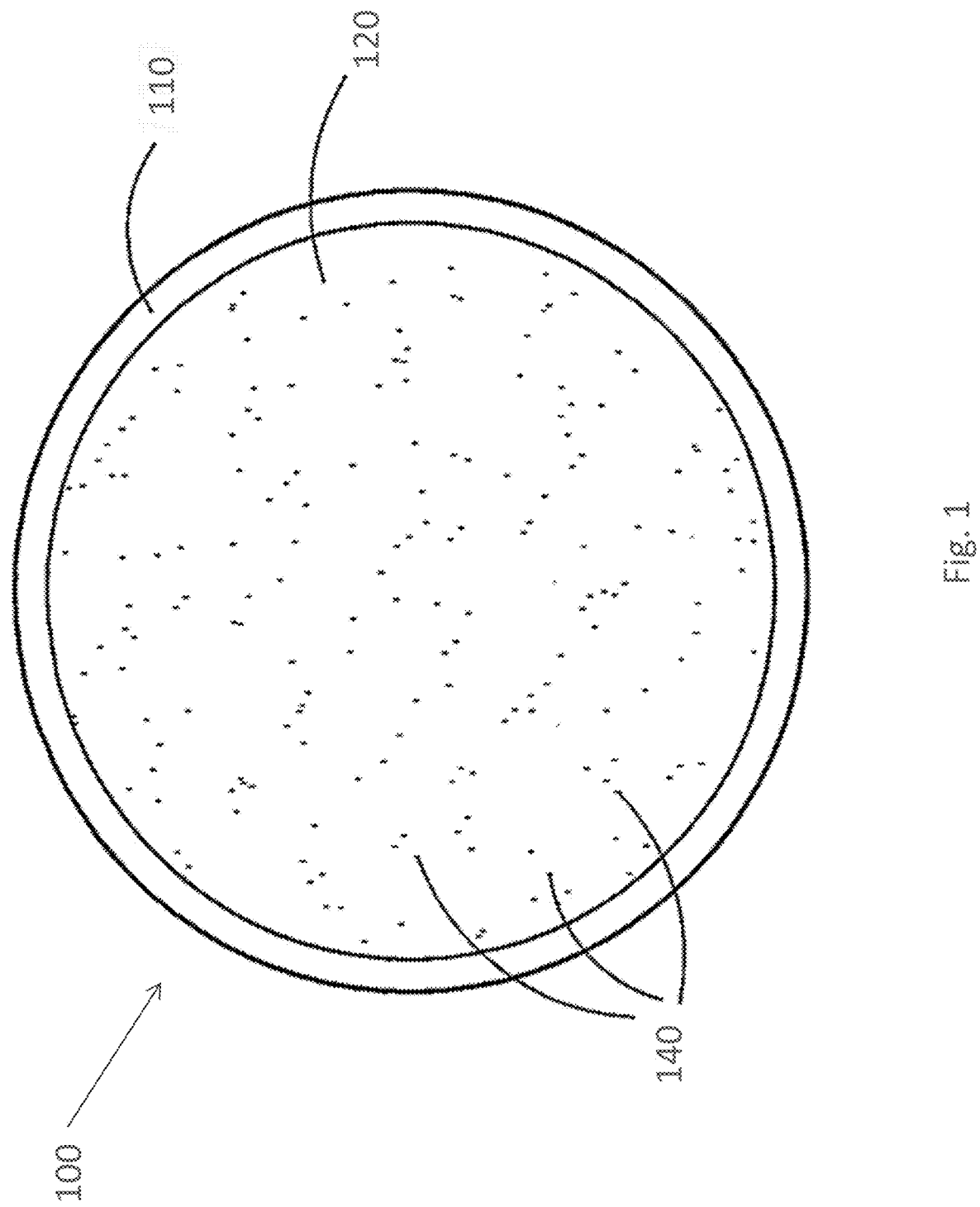
FIG. 1 shows a non-limiting example of an illustrative prosthetic implant according to at least some embodiments of the present invention.

The present invention provides a composite implant material comprising a base material mixed with additives. The implant material has improved radiology characteristics such as improved radiolucency and decreased associated visual noise from ultrasonography. The definition of the implant shell, when imaged using ultrasound, is preferably improved through use of a composite material immediately adjacent to the shell that is hyperechoic. As echoes are created by the differences in conduction speed of sound waves, hyperechoic implant material is created through the maximum reduction in the speed of sound. The implant therefore preferably comprises low density additives such as hollow additives or additives that include gas. Preferably, the additives have a partial or complete vacuum, making the echo even stronger, as there are less sound conducting molecules.

The material of the present invention is more radiolucent than pure silicone gel, when viewed for example in a mammogram, improving the visibility of tissue in front of or behind the implant and therefore improving the diagnostic capability of the physician or radiologist. The material preferably comprises additives suited for radiology such as those that are radiolucent such as less dense elements which are hollow, porous or gaseous. Optionally, additive materials are used that are relatively transparent to x-rays where the x-ray settings (voltage and milliamps) used are those commonly used in imaging studies. A non-limiting example of x-ray voltages are those typically used in mammography of between 24 kV-32 kV.

A non-limiting example of a radiolucent material optionally used as an additive is polyether ether ketone (PEEK) as in Kurtz S M, Devine J N. (PEEK Biomaterials in Trauma, Orthopedic, and Spinal Implants. Biomaterials. 2007; 28(32):4845-4869. doi:10.1016/j.biomaterials.2007.07.013.) "PEEK is now broadly accepted as a radiolucent alternative to metallic biomaterials in the spine community."

The composite material of the current invention preferably includes additives such that, in case of rupture, the extravasated composite material of the present invention is easily identifiable using imaging technology and distinguishable from physiologic aberrations such as cysts, whether intracapsular or extracapsular due to the presence of the additives. As a non-limiting example, hyperechoic particles have the advantage that they are easy to identify if they leak from the implant, indicating a ruptured implant. Alternatively the additives may be hypoechoic. The hyperechoic or hypoechoic additive preferably changes the conduction speed of the base material by between 5%-20%.

For a base material comprising a solvent, the additives in the implant material reduce the total amount of free molecules resulting in the reduction of the concentration gradient and therefore in free molecule bleed. As described above, the concentration gradient is the driving force for free molecule bleed and therefore reducing the free molecule concentration reduces gel bleed. Preferably the additives reduce the free molecule concentration in the base material by between 5%-95%. The reduced free molecule concentration is measured by comparing the free molecule concentration of the base material with no additives compared to the free molecule concentration of the composite material. A non-limiting example of the improvement is shown in the pictures and graphs presented in FIGS. 6A and 6B.

Further, if there is bleed from the implant, the remaining additives limit the total amount of liquid that can be removed using the two mechanisms as described above. By contrast, prior art implants are not constrained and can theoretically lose a high percentage of their liquid to diffusion.

The additives in the implant material increase the cross-linking density/cohesion of the base material, thus strengthening the base material while maintaining its integrity. Preferably the additives are selected to enhance the mechanical properties such as increasing the Elastic Modulus (G') by 20%-1000% or 5000% or more. A non-limiting example of the improvement is shown in the graphs presented in FIG. 7. Alternatively, the increase in cohesiveness is measured by a penetration test, comprising placing a weighted shaft with a plate on the surface of the tested material and measuring how deeply it has sunk after a certain amount of time. Preferably, the additives increase the cohesiveness as measured by a penetration test such that the penetration into the composite material is 5%-99.5% shorter than into the base material.

These improvement and others are preferably provided by the addition of additives to base material as a volume substitution element creating a two phased system with a continuous phase and a dispersed phase or bi-continuous system.

The implant material is preferably contained within a shell to form an encapsulated prosthetic implant. A non-limiting example of a suitable shell material is a silicone elastomer, optionally with a material such as polyurethane foam overlaid on the shell. At least the shell, but preferably all of the materials of the implant, is biologically compatible and safe for therapeutic and/or cosmetic use internally to the human body.

The above described base material is preferably a silicone gel as is known in the art, such as PDMS and derivatives thereof for example. Alternatively, the base material is a polyurethane network. Alternatively the base material is any other suitable biocompatible base material or combination of base materials.

Optionally the base material is chosen such that it may form covalent bonds with the chosen additive which may be any one of the additives described herein.

The additive or combination of additives is preferably chosen based on factors including but not limited to biocompatibility, durability, price, and other factors.

The additive optionally comprises one or more materials such as glass, ceramic, metal, polymers, such as PMMA (polymethyl methacrylate), polyacrylonitrile, polybutadiene, polyether ether ketone (PEEK) (or any other natural or synthetic rubber or similar materials) for example, or any other amorphous or semi-crystalline polymer. The materials may optionally be determined according to their relative flexibility. For example, for PMMA, the tensile strength at yield is preferably from 52 to 71 mega-Pascal and the tensile modulus is preferably from 2.2 to 3.1 giga-Pascal. As a further example, for Borosilicate glass (Pyrex®) with 80% silica, 13% Boron and salts, the tensile strength at yield is preferably between 35 to 100 mega-Pascal and the tensile modulus is $64*10^3$ mega-Pascal.

Optionally the additive comprises rubber. Non-limiting examples of suitable rubber include: Ethylene-acrylate Rubber, Polyester Urethane, Bromo Isobutylene Isoprene, Polybutadiene, Chloro Isobutylene Isoprene, Polychloroprene, Chlorosulphonated Polyethylene, Epichlorohydrin, Ethylene Propylene, Ethylene Propylene Diene Monomer, Polyether Urethane, Perfluorocarbon Rubber, Fluoronated Hydrocarbon, Fluoro Silicone, Fluorocarbon Rubber, Hydrogenated Nitrile Butadiene, Polyisoprene, Isobutylene Isoprene Butyl, Acrylonitrile Butadiene, Polyurethane, Styrene Butadiene, Styrene Ethylene Butylene Styrene Copolymer, Polysiloxane, Vinyl Methyl Silicone, Acrylonitrile Butadiene Carboxy Monomer, Styrene Butadiene Carboxy Monomer, Thermoplastic Polyether-ester, Styrene Butadiene Block Copolymer, Styrene Butadiene Carboxy Block Copolymer.

The additive may optionally be of any suitable size. Each additive is optionally between 1 nm (nanometer) and 1 mm. Preferably, the additive is no bigger than 500 microns. Preferably, the packing factor of the additives may be increased by using polydispersity of additive sizes. Preferably, the additives comprise particles of a plurality of different sizes, optionally of at least 20% difference between them.

The additive may optionally comprise any three-dimensional shape. Non limiting examples of additive shapes optionally include spherical, fibrous, platelet, flake, amorphous, crystalline, semi-sphere, rod, disk or combinations of these shapes or irregular versions of these shapes. Each additive may optionally have an internal or external structural element(s), or a combination thereof, for maintaining the three-dimensional shape of the additive, including but not limited to a beehive, etc.

The additives may optionally be hollow or may be completely solid. Hollow additives preferably comprise a shell that ranges in thickness from a monolayer of atoms to 95% of the radius of the additive. Hollow additives may optionally be filled with a gas. Optionally, the additives may be porous, having holes or pores with varying tortuosity within the additive that can be filled with the base material or other material. Porous additives preferably comprise a solid component that ranges in thickness from a monolayer of atoms to 95% by radius of the additive.

The additive may optionally be a composite of several materials. These materials may optionally be arranged in multiple layers where subsequent layers enclose inner layers or alternatively may be arranged such that the separate layers are in contact with the surrounding base material. The additives may optionally comprise a plurality of stacked layers, whether flat or with curvature; in the latter case, the curvature is preferably determined according to the implant shape. Non-limiting examples of materials that may be combined include glass, ceramics, metals, plastics, and rubbers. For example a glass micro-sphere may be covered with a layer of rubber. More preferably, a blend of polymers is used, for example a blend of a polymer such as PMMA and a rubbery material such as polybutadiene for example.

The additive optionally has varying surface roughness. Optionally, the RMS roughness varies between 0.2 nm and 40 nm.

Optionally, the additive is a non-solvent liquid such as an oil that forms bubbles inside the base material. Non-solvent liquids of varying viscosities may optionally be used. Optionally, the additive is a non-silicone gel such as a hydrogel.

Optionally, the additive is a gas. Preferably the gas is inert such as nitrogen. Optionally, the gas may comprise oxygen or carbon dioxide. Optionally, the gas is formed as micro-lumens, which may optionally comprise rigid materials, including but not limited to glass, ceramic, etc. Optionally, the micro-lumens are enclosed by a rigid material such as rigid plastic. A non-limiting example of a rigid plastic is Polyether ether ketone (PEEK).

The additives optionally incorporate varying surface interactions from inert to chemical bond interactions with the surrounding base material. Optionally, the additives are free floating, i.e.: not bonded to the base material, and are mechanically constrained by the base material. Optionally, the additives are bonded to the base material with weak bonds such as van der Waals, hydrogen bonds, or ionic interactions. Preferably, the additives are bonded to the base material using chemical covalent bonds. The bonds preferably prevent the base material and the additive(s) from separating into two phases.

The additives are preferably surface treated to enable better bonding with the surrounding base material and prevent slippage or separation into two phases. Also the bonding of additives to the base material causes the base material to surround the additives; in the event of rupture or leakage, without wishing to be limited by a single hypothesis, it is expected that the base material will continue to cover the additives, such that the body would only be exposed to the base material.

Non-limiting examples of surface treatments include: surface anchored long molecular weight chains such as stearic acid, or any other long organic chain, or polymer brushes, hydrophobic or hydrophilic molecules and other such molecules; creation of a charged surface that favors electrostatic attraction for example by the addition of poly-electrolyte to silicone gel; increasing the "roughness" or physical variability of the surface of the additives, such that parts of the surface project out into the base material and hence may interact with the base material; or use of silanes with additives, for example, glass. The organofunctional group of the silane is selected according to the type of interaction that is favorable between the base material and the additive.

Preferably one interface material is used to surface treat the additives. Optionally one or more than one coupling agent is used as a surface treatment with successive coupling agents added on top. Preferably two coupling agents are used. Optionally up to 20 coupling agents may be used. Most cases of surface treatment by organofunctional silanes, zirconates, titanates and other coupling agents result in a polymer-surface interaction. The type of coupling agent is selected according to the surface chemistry of the additive and the chemistry of the base material.

Various other surface treatments and methods for applying these are taught in U.S. patent application Ser. No. 13/520,356, filed on Jul. 3, 2012, hereby incorporated by reference as if fully set forth herein, which is co-owned in common with the present application and which has at least one inventor in common, may also optionally be used, additionally or alternatively.

Optionally, the additives are provided in different concentrations in different areas of the implant. As a non-limiting example, additives adapted for use in ultrasound can have a higher concentration just adjacent to the shell to create a strong echo as described above. As a further non-limiting example, additives adapted for use in mammography can have a higher concentration in the internal parts of the implant in order to create a high degree of radiolucency in the implant.

As a further non-limiting example, additives can have a higher concentration in internal parts of the implant in order to create a diffusion gradient aimed inwards. As a further non-limiting example, additives can also have higher concentration close to the shell in order to serve as a barrier/buffer for diffusion.

As a further non-limiting example, additives can have a higher concentration in internal parts of the implant in order to create a less rigid implant material closer to the surface.

Optionally, additives have the same density as the base material or alternatively, they have a greater density. Additives preferably have a lower density than the surrounding base material.

Preferably, the additives combine any of the characteristics from those listed above to allow a range of embodiments of the present invention encompassing additives of combined and varied sizes, shapes, densities, materials, and structures, with a chosen bonding mechanism to the base material.

The principles and operation of the present invention may be better understood with reference to the drawings and the accompanying description.

Figure 2:
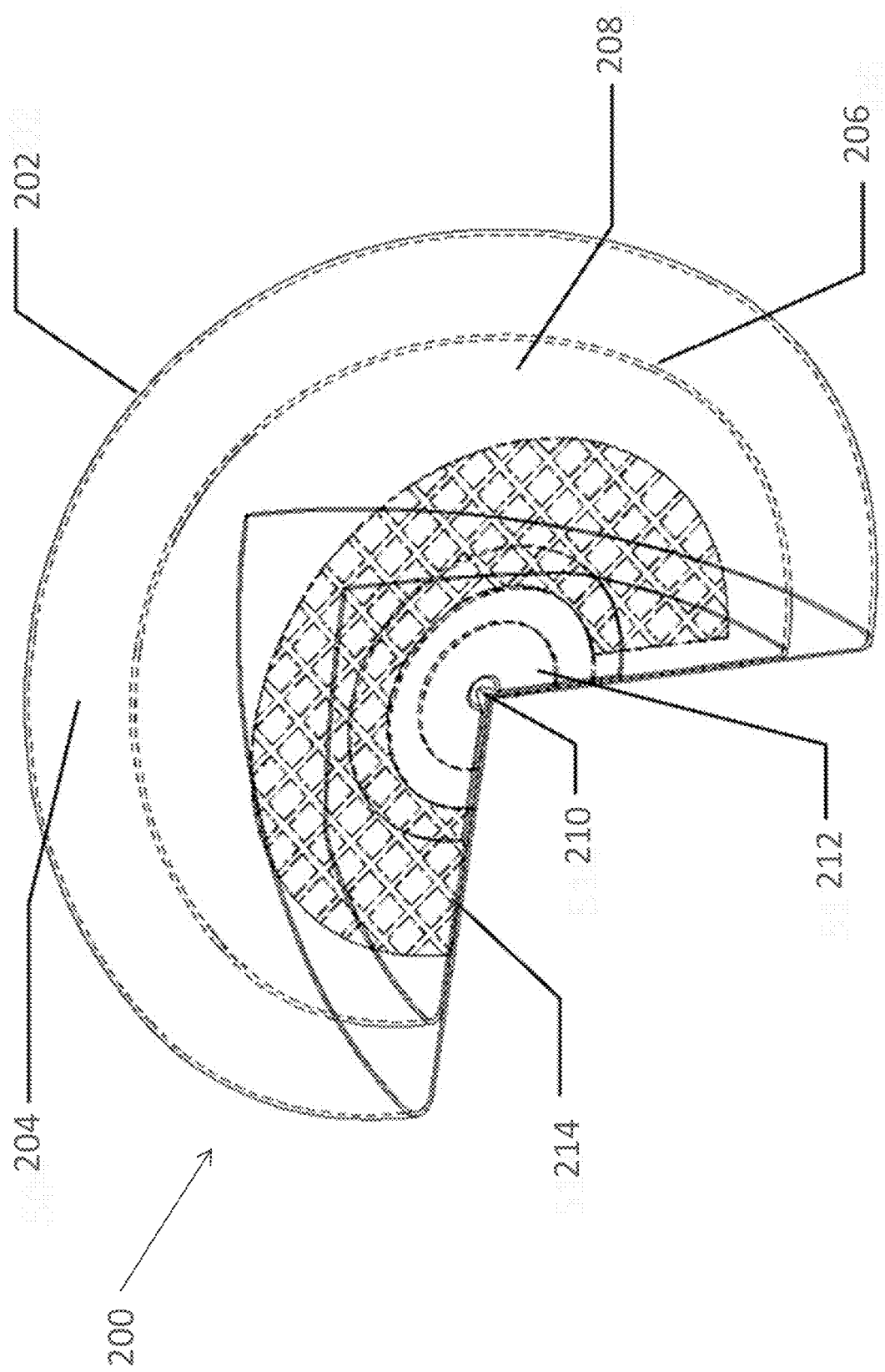
FIG. 2 shows another non-limiting example of an illustrative prosthetic implant according to at least some embodiments of the present invention.

Reference is now made to FIGS. 1 and 2 which show non-limiting exemplary embodiments of implants according to the present invention. Any of the above described characteristics of shell material, base material and additives or combinations thereof may optionally be used with the below described structures.

FIG. 1 shows a non-limiting example of an illustrative encapsulated prosthetic implant according to at least some embodiments of the present invention. As shown, an implantable prosthesis 100 comprises a low penetratable shell 110 that optionally comprises a biocompatible silicone, polyurethane or other material as is commonly used for implants. Shell 110 may comprise a single layer or multiple layers, wherein some layers may be from one material and others from another. Additionally, shell 110 may be smooth or textured, with various patterns. Shell 110 can have areas of varying elasticity. Shell 110 can have a different thickness in different areas. Optionally, the material of shell 110 may be a combination of several materials. Generally, shell 110 serves as an enclosure for preventing part or all of the content of prosthesis 100 from leaking out. Optionally, shell 110 may be provided in various shapes, for example round, oval, anatomical, custom or other.

Shell 110 contains a base material 120 and at least one additive 140. In this non-limiting example, shell 110 contains a plurality of additives 140, which may optionally comprise any of the characteristics described above. Optionally, the additives are distributed uniformly throughout the base material 120. Optionally, the additives are provided in different concentrations in different parts of the base material 120.

Reference is now made to FIG. 2 which shows a partially cut-away view of another non-limiting example of an illustrative encapsulated prosthetic implant 200 according to at least some embodiments of the present invention. In this example, an outer shell 202 contains an outer composite material 204, while an inner shell 206 contains an inner composite material 208. Each of outer shell 202 and inner shell 206 may optionally be constructed from a silicone elastomeric material as described herein, optionally with a plurality of layers and also optionally with a barrier layer. Outer shell 202 may optionally feature any of a smooth, non-textured surface; a textured surface; or a micro polyurethane foam coated surface. Surface texturing has been shown to reduce the incidence and severity of capsular contraction. Inner shell 206 is preferably smooth but may also optionally be textured.

Outer composite material 204 preferably features additives adapted for use in ultrasound which have a higher concentration to create a strong echo as described above. Inner composite material 208 preferably features additives adapted for use in mammography with a high degree of radiolucency as described above.

Alternatively, outer composite material 204 preferably features additives having a higher concentration close to the shell in order to serve as a barrier/buffer for diffusion as described above. Inner composite material 208 preferably features a higher concentration of additives as the distance from inner shell 206 increases in order to create a diffusion gradient aimed inwards as described above.

Alternatively, outer composite material 204 preferably features a lower concentration of reinforcing additives to create a less rigid implant material closer to the surface. Inner composite material 208 preferably features a higher concentration of additives and therefore greater reinforcement. Alternatively, inner composite material 208 features a higher concentration of additives as the distance from inner shell 206 increases Optionally, each of outer shell 202 and inner shell 206 is closed with a patch made of the same silicone elastomers as the respective shell 202 and 206, and glued using an adhesion component, with small silicone cap 210 on the inner side of the posterior patch 212, used for filling the implant with the composite material. Optionally. Inner shell 206 is situated concentrically within outer shell 202 and glued to it at a base 214.

Various other arrangements of the shell and/or other components which are taught in U.S. patent application Ser. No. 20090299473, filed on Apr. 24, 2006, hereby incorporated by reference as if fully set forth herein, which is co-owned in common with the present application and which has at least one inventor in common, may also optionally be used, additionally or alternatively.

Figure 3B:
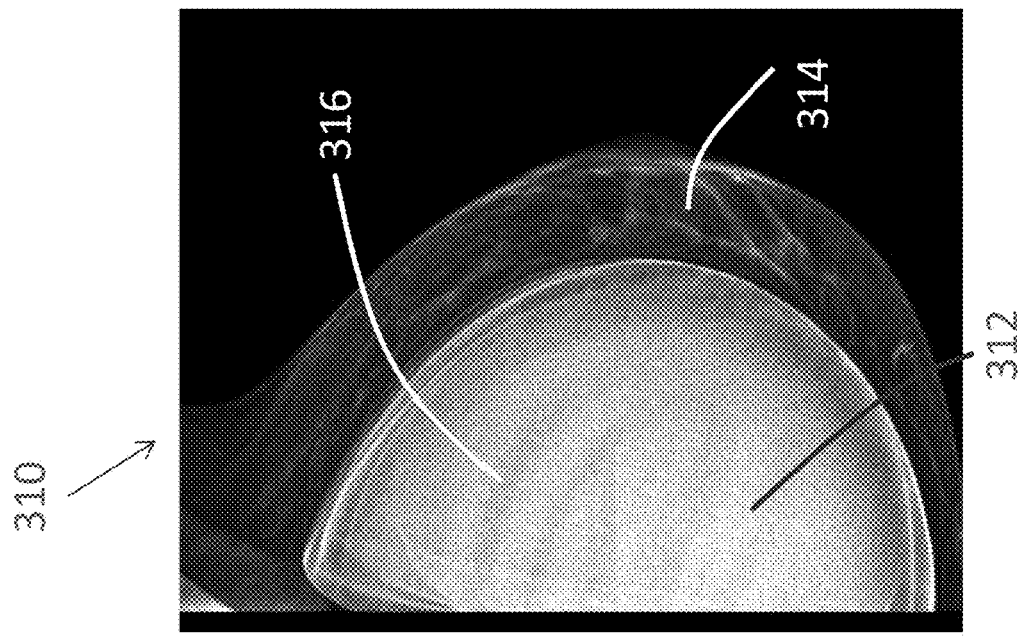
FIGS. 3A-3E show mammography images of breasts and breast tissue with a prior art implant and with the implant of the presently claimed invention.
Figure 3A:
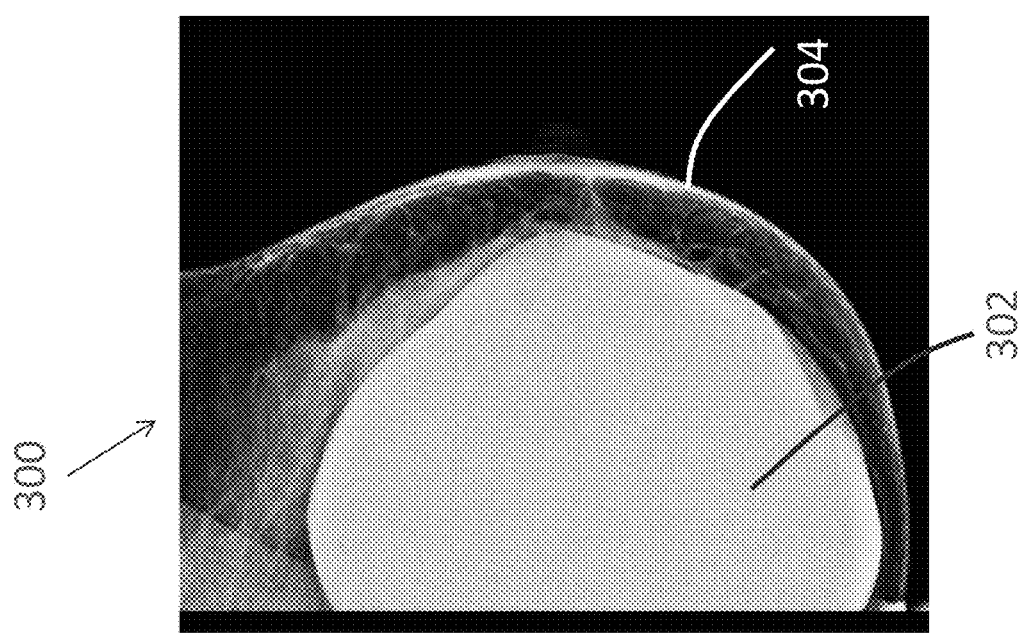

Reference is now made to FIGS. 3A and 3B which are mammography images of respectively a breast with a prior art implant and a breast with the implant of the presently claimed invention. As shown in the mammogram 300, the prior art implant 302 appears completely white (opaque to x-ray) showing no detail of the tissue in front of it or behind it. Breast tissue 304 not obscured by the implant is visible in the mammogram 300.

By contrast, in the mammogram 310 of the breast 314 with the implant 312 of the presently claimed invention, tissue 316 of the breast is visible through the implant 312 due to the presence of radiolucent additives as described above.

Figure 3D:
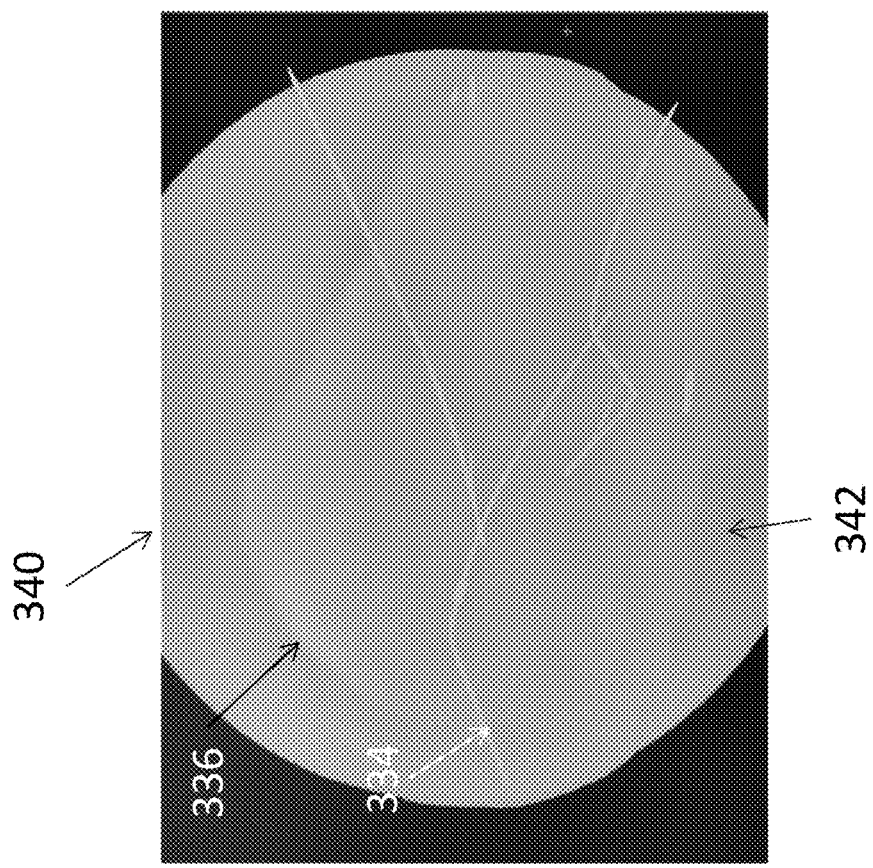
Figure 3C:
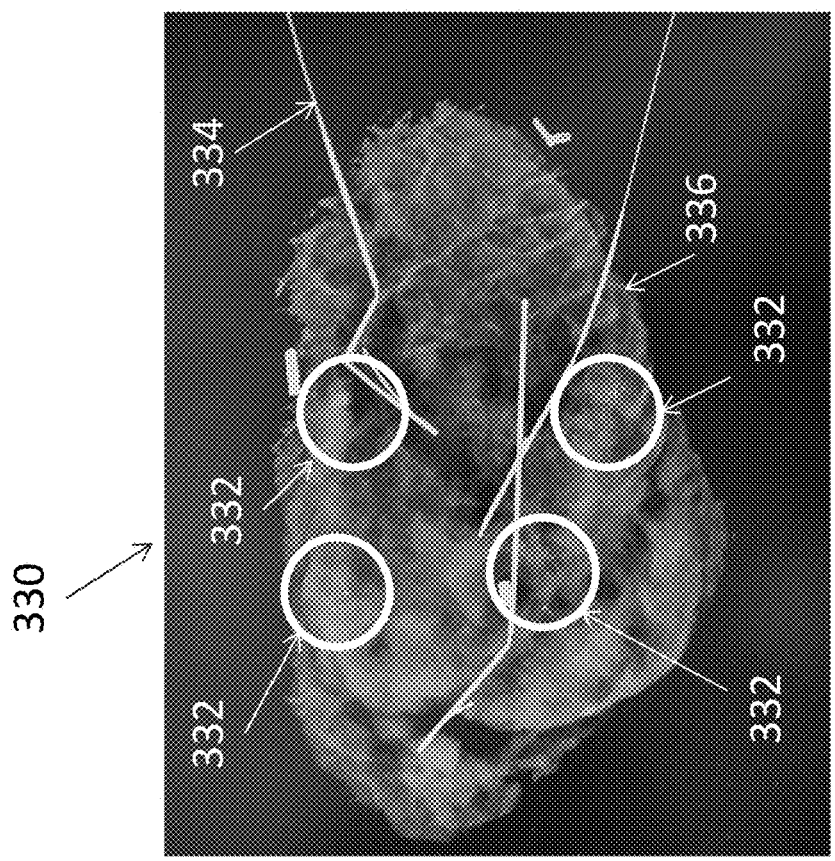
Figure 3E:
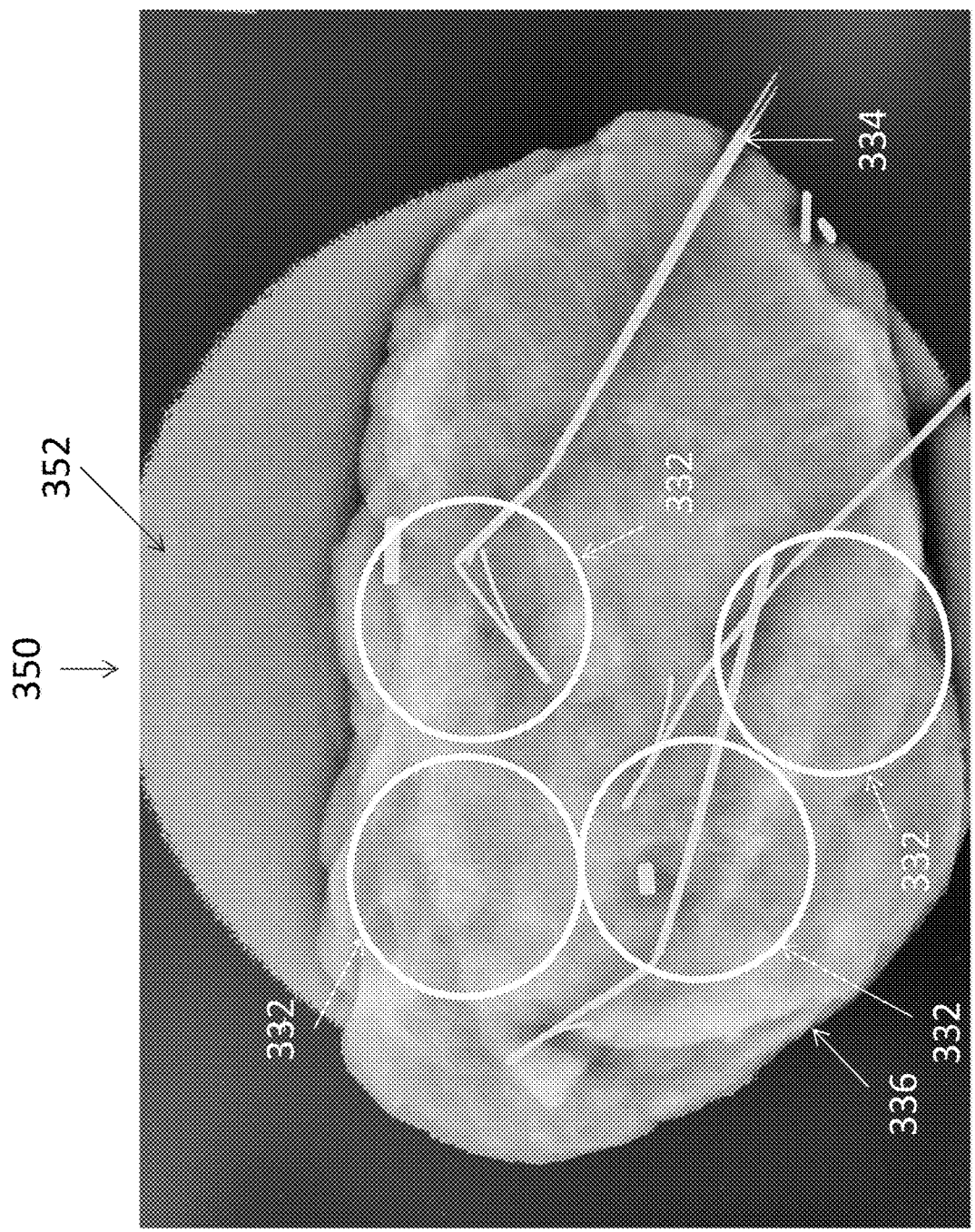

Reference is now made to FIGS. 3C and 3D which are x-ray images of excised breast tissue following a lumpectomy from a patient in which microcalcifications were identified. As shown in FIG. 3D, the excised tissue 336 is almost completely obscured by the prior art implant 342. In the x-ray image 350 of FIG. 3E, the same x-ray machine and method have been used with the implant 352 of the present invention placed above the excised tissue 336. In image 350 the calcifications are visible and are indicated by circles 332. It is therefore possible to diagnose the presence of cancerous tissue with an implant 352 of the present invention implanted in the patient without the use of implant displacement techniques. Optionally implant displacement techniques are used for imaging of tissue with the implant of the present invention wherein the implant preferably enables clearer imaging of tissue areas where the implant cannot be moved out of the radiography image by the implant displacement technique.

Figure 4B:
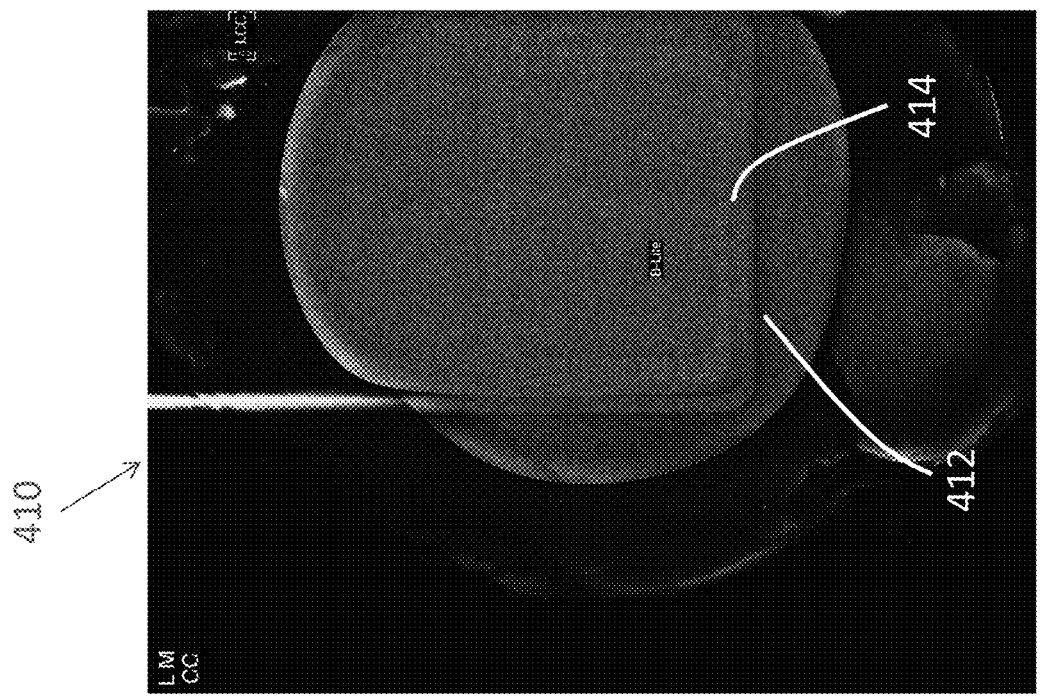
FIGS. 4A and 4B show mammography images of a prior art implant and the implant of the presently claimed invention placed on top of a marked localization paddle and a turkey breast.
Figure 4A:
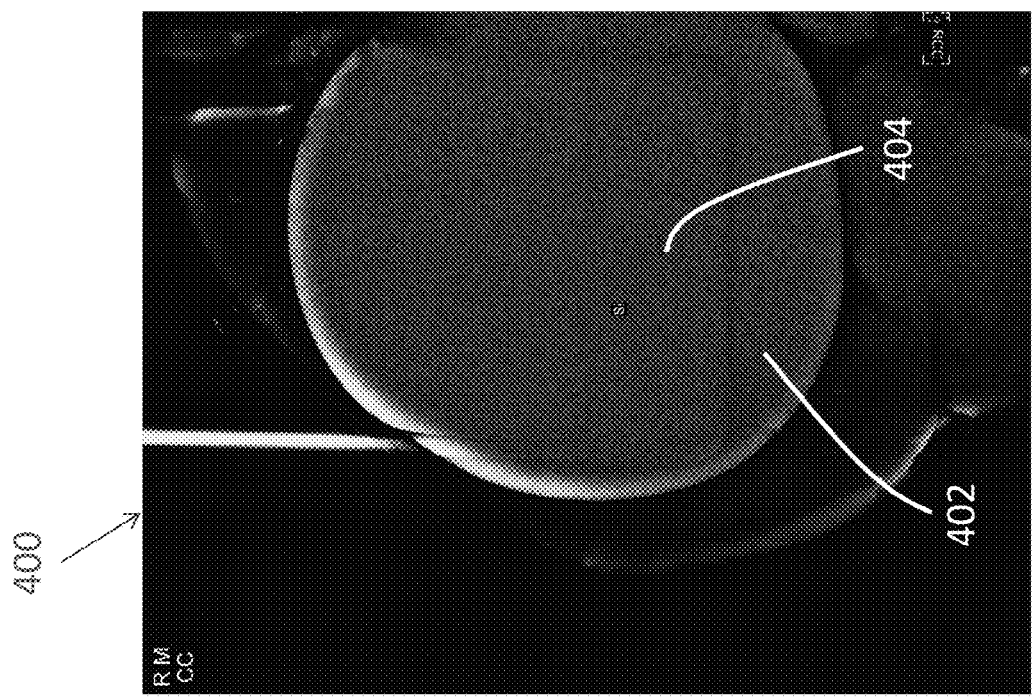

Reference is now made to FIGS. 4A and 4B which are mammography images of breast implants on top of a marked localization paddle and a turkey breast. FIG. 4A shows a prior art implant and FIG. 4B shows an implant according to the presently claimed invention. Both mammograms were performed under the same thickness and exposure parameters.

As shown in FIG. 4A, in mammogram 400, prior art implant 402 almost completely obscures localization paddle 404. By contrast, in FIG. 4B, mammogram 410 shows the implant 412 of the presently claimed invention, where the lettering on localization paddle 414 is visible through the implant 412. This is due to the radiolucency of the additives in implant 412 as described above.

Figure 5B:
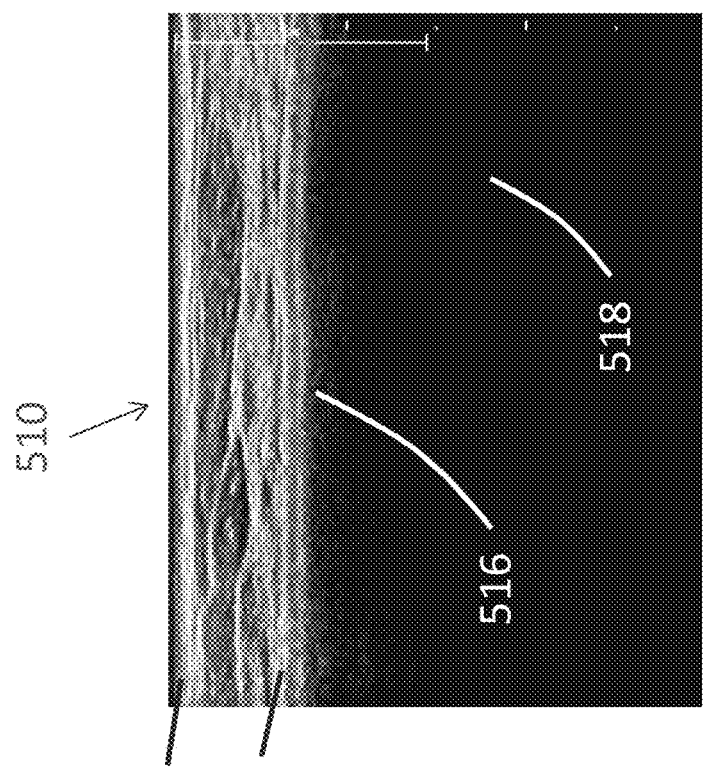
FIGS. 5A-5F show ultrasound images of breasts with prior art implants (5A, 5C) and implants of the presently claimed invention (5B, 5D).
Figure 5A:
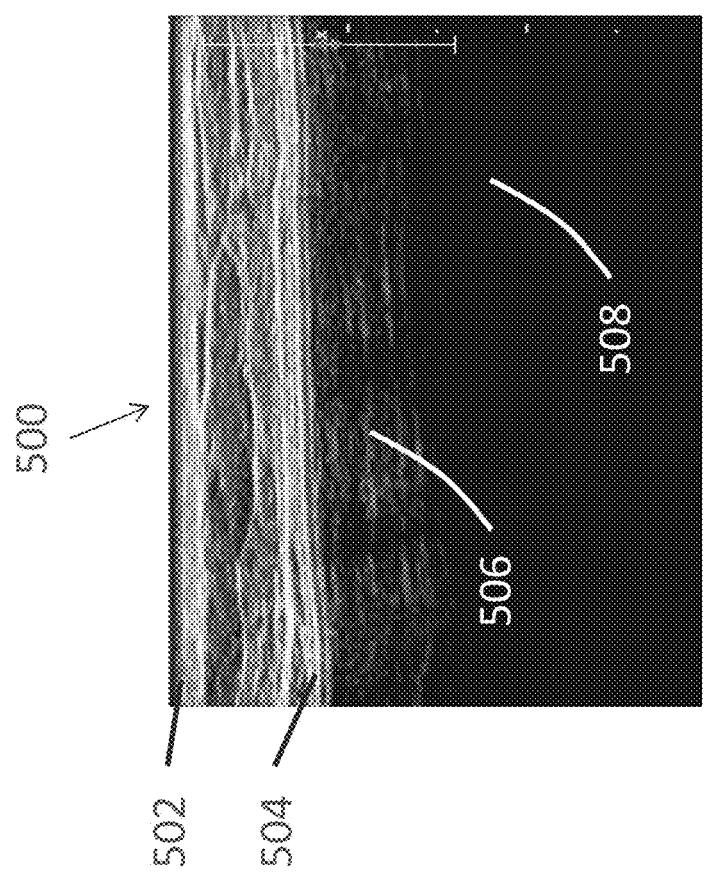
Figure 5D:
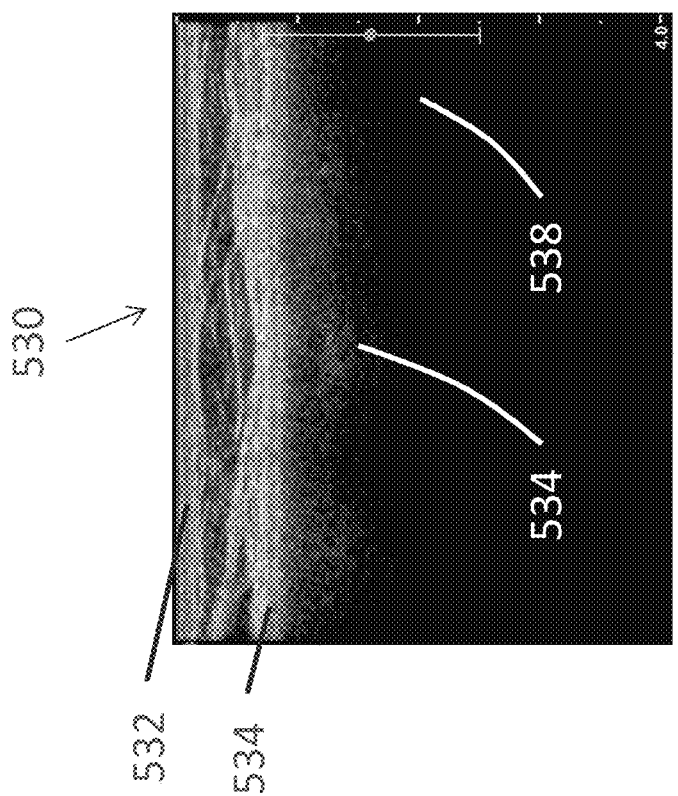

Reference is now made to FIGS. 5A-5D which are ultrasound images of breasts with prior art implants (5A, 5C) and implants of the present invention (5B, 5D). As shown in FIG. 5A, the shell 502 of a prior art implant is visible in an ultrasound image 500 captured with a 12 MHz probe.

The top of image 500 is the interface of the probe with the skin. Then there is a representation of tissue 502 comprising skin, fat, glands and other tissue, followed by the shell of the silicone implant 504. The gel 508 is seen as the black area. Reverberations seen as visual noise 506 caused by the implant are also visible in image 500 in the area which should be black (the gel 508). This noise is seen extending 1.5 cm into the area of the image 500. The noise also extends above the shell creating a cloud like snow over the tissue area 502 of the image which is intended for diagnosis.

By contrast, the 12 MHz ultrasound 510 of the breast with the implant of the presently claimed invention, shows very little visual noise 516, and the tissue 512, shell 514, and implant material 518 are not obscured by noise as found in ultrasound 500.

Figure 5C:
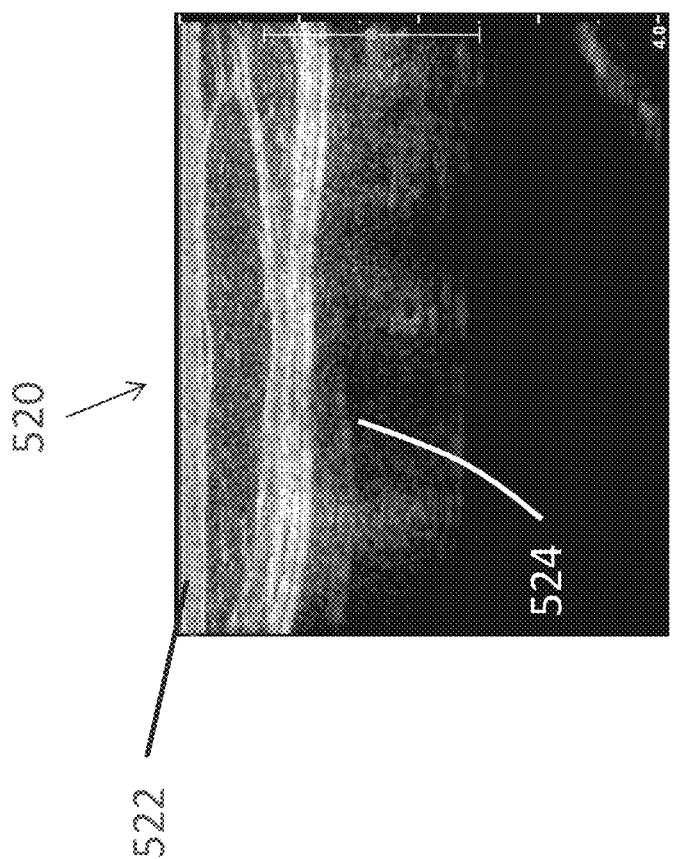

Similarly, FIG. 5C shows an ultrasound image 520 captured with a 17 MHz probe where both the implant shell 522 and the visual noise caused by the implant 524 are visible. The echoic borders at the interface of shell 522 appear thick, presenting a shell that is thicker than it actually is to the radiologist. By contrast, the 17 MHz ultrasound 530 of the breast with the implant of the presently claimed invention, shows far less visual noise 534, and the tissue 532, shell 534, and implant material 538 are not obscured or distorted by noise as found in ultrasound 520.

Figure 5F:
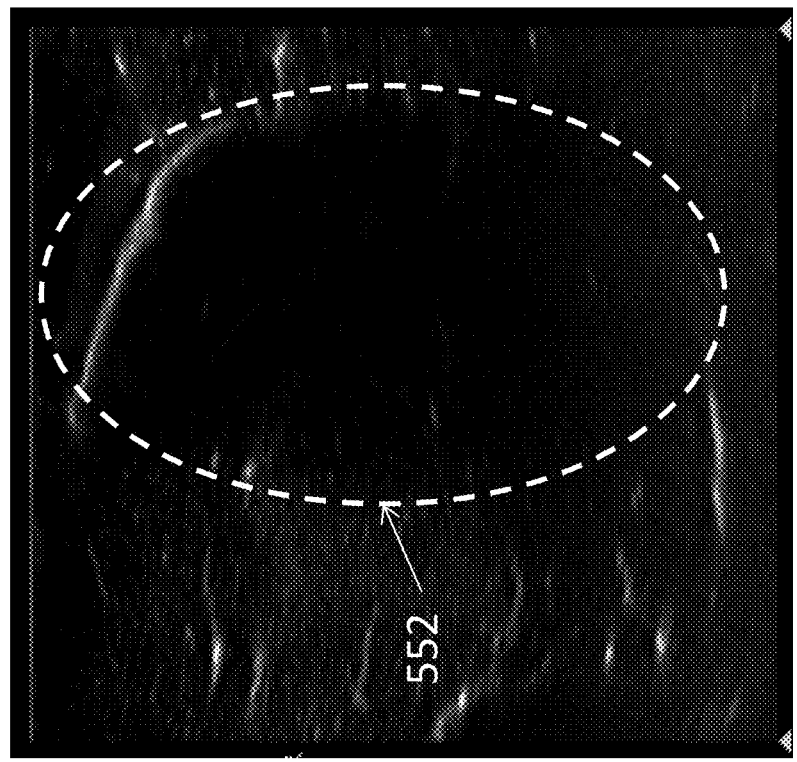
Figure 5E:
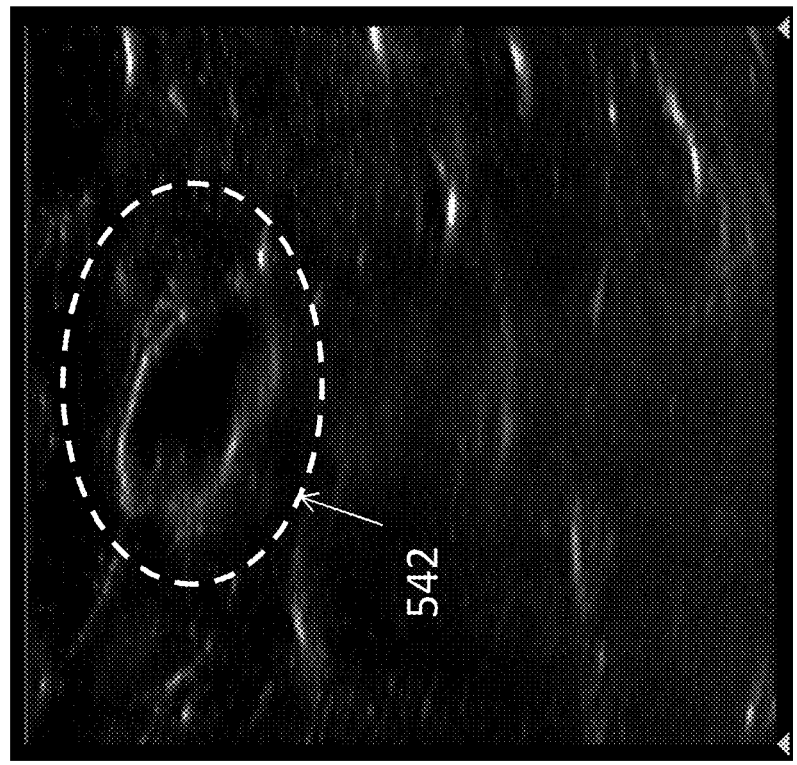

Reference is now made to FIGS. 5E-5F which are ultrasound images of tissue with prior art implant material, in this case silicone (5E) and implant material of the present invention (5F). As described above, in the case of extravasated implant material such as when the implant ruptures, the silicone of prior art implants appears as a cyst or tissue as shown in FIG. 5E. By contrast, as shown in FIG. 5F, extravasated composite material of the present invention is easily identifiable using imaging technology and distinguishable from physiologic aberrations such as cysts, whether intracapsular or extracapsular due to the presence of the additives. In an ultrasound image 550, the implant material of the present invention shows as a light line and primarily as a shadow (indicated by circle 552) that is easily identifiable to a radiographer and will not be confused with a tissue anomaly such as a cyst. Therefore in a case of rupture the implant material can be easily identified by ultrasound due to the hyperechoic or hypoechoic additives which provide strong differentiation to the surrounding tissue.

Figure 6A:
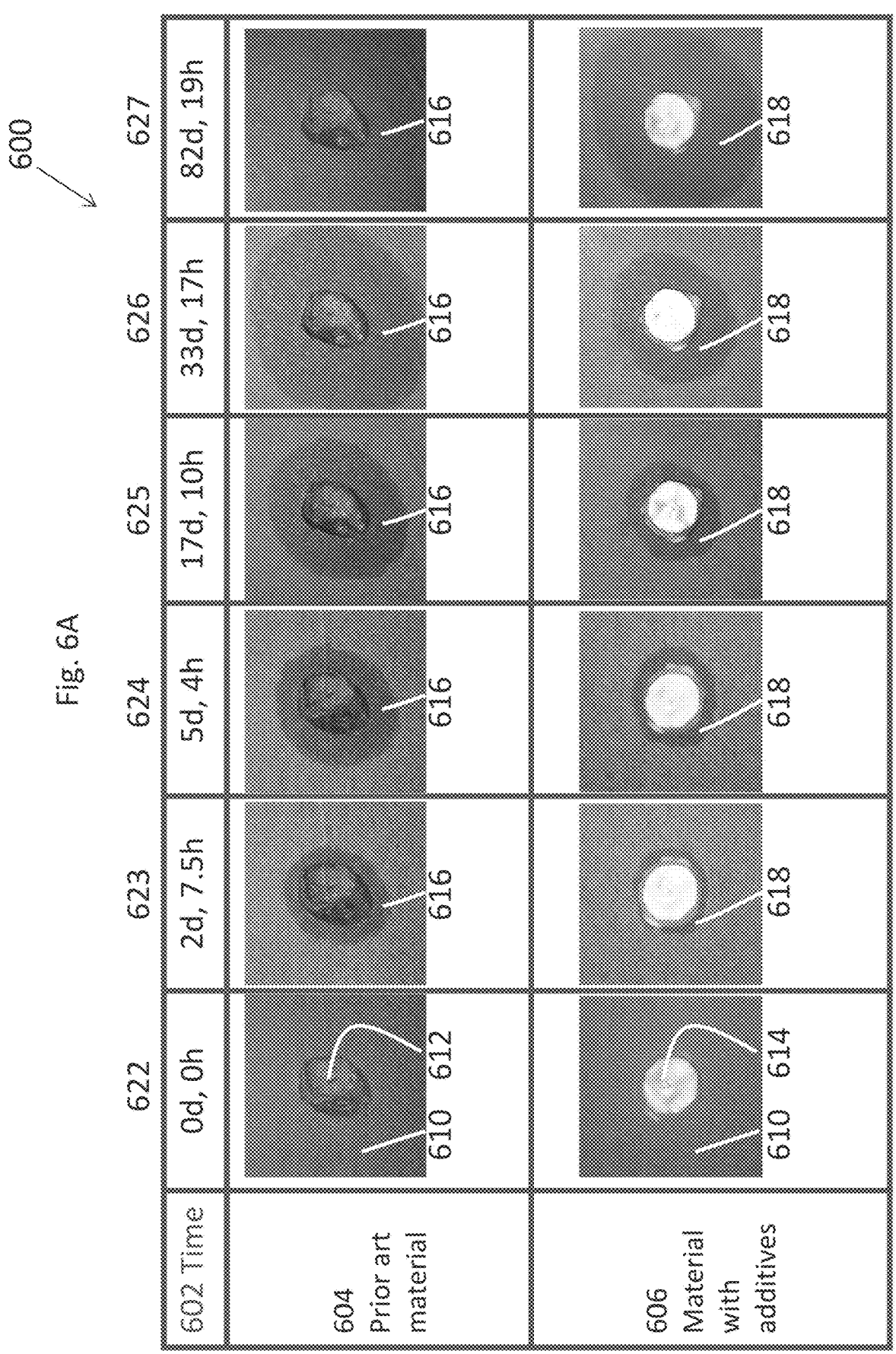

Reference is now made to FIGS. 6A-6B which are photographs and a graph showing comparative solvent diffusion of a prior art implant gel and the composite implant material of the presently claimed invention. FIG. 6A shows a table 600 with rows as follows: time elapsed row 602, prior art gel row 604 and composite implant material row 606. Each of rows 604 and 606 show progressive photographs of equal sized samples of gel/composite material laid on absorbent paper 610. Gel 612 is from a prior art implant and composite material 614 is the composite implant material of the presently claimed invention comprising additives to reduce diffusion.

Column 622 shows photographs taken at time=0, i.e.: immediately after setting the gel/material in place; Column 623 shows the same materials photographed after 2 day and 7.5 hours; Column 624 shows the same materials photographed after 5 days and 4 hours; Column 625 shows the same materials photographed after 17 days and 10 hours; Column 626 shows the same materials photographed after 33 days and 17 hours; and Column 627 shows the same materials photographed after 82 days and 19 hours.

FIG. 6B shows a graph 650 that plots the elapsed time 602 (in hours) against the calculated wetted area 652 (in mm$^2$) of the absorbent paper 610 as shown in the photographs of FIG. 6A.

As shown in column 623 after 2 days and 7.5 hours, solvent from prior art gel 612 has diffused significantly more than solvent from the composite material 614 of the presently claimed invention. The difference is evident from the greater diameter of diffused prior art solvent 616 compared to the diameter of diffused solvent 618 from the presently claimed invention. Similarly, in columns 624-627 solvent from prior art gel 612 has diffused significantly more than solvent from the composite material 614 of the presently claimed invention. Graph 650 shows the greater diffusion of prior art gel solvent (line 654) compared to the solvent in the composite material of the presently claimed invention (line 656).

It should be noted that the absorbent paper 610 is not comparable to the human body since the solvent (on the paper) is not removed and therefore the rate of diffusion (on the paper) is actually slowed. In the human body, a large portion of the solvent is removed or spreads through various biological mechanisms and the diffusion gradient remains high. Nevertheless, the absorbent paper 610 illustrates the significant difference between the prior art and the composite material of the current invention.

Over a longer time therefore, there are significant differences in the amount of total solvent that can be potentially released into the body. The composite material of the presently claimed invention has a slower rate of diffusion and a significantly smaller overall amount of solvent to release. This could potentially show up as less likelihood of lymphadenopathy, even in case of a rupture.

Figure 7:
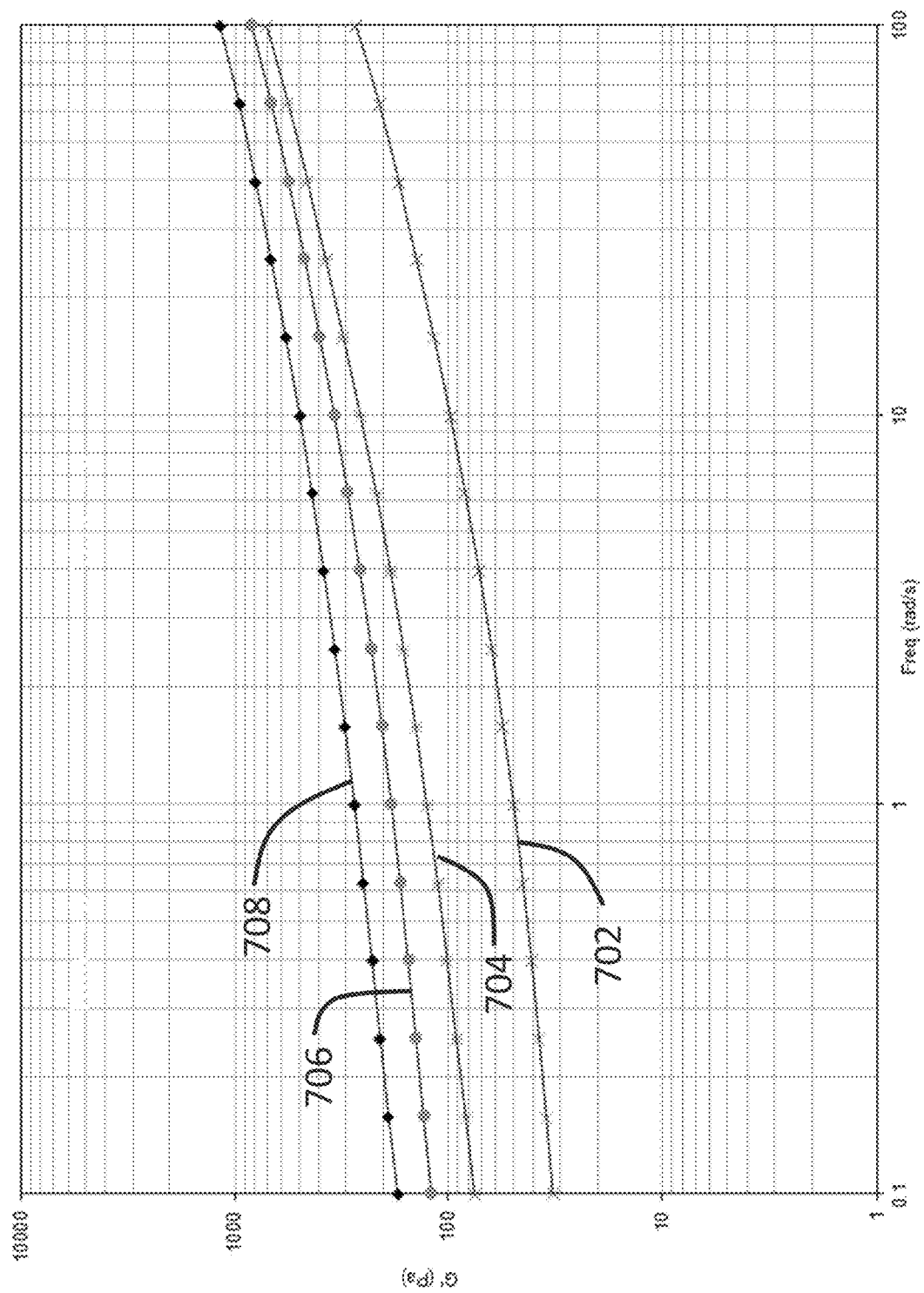
FIG. 7 is an exemplary rheology graph showing comparative elastic modulus of a prior art implant gel and three alternative composite materials as per the presently claimed invention.

Reference is now made to FIG. 7 which is a set of rheology graphs showing comparative elastic modulus of a prior art implant gel and three alternative composite materials as per the presently claimed invention. Rheological characterization provides a measure of storage modulus (G') as a function of shear rate (frequency measured in Hz or rad/s). The graph shows rheological characteristics for four different materials where 702 is a rheology graph for a prior art implant gel and 704, 706 and 708 are rheology graphs for implant materials of the presently claimed invention—each comprising different additives in different concentrations.

As shown, the implant materials of the presently claimed invention display increasing elastic modulus compared to the prior art implant gel (graph 702), with the composite material of graph 708 showing the most increased elastic modulus.

Figure 8A:
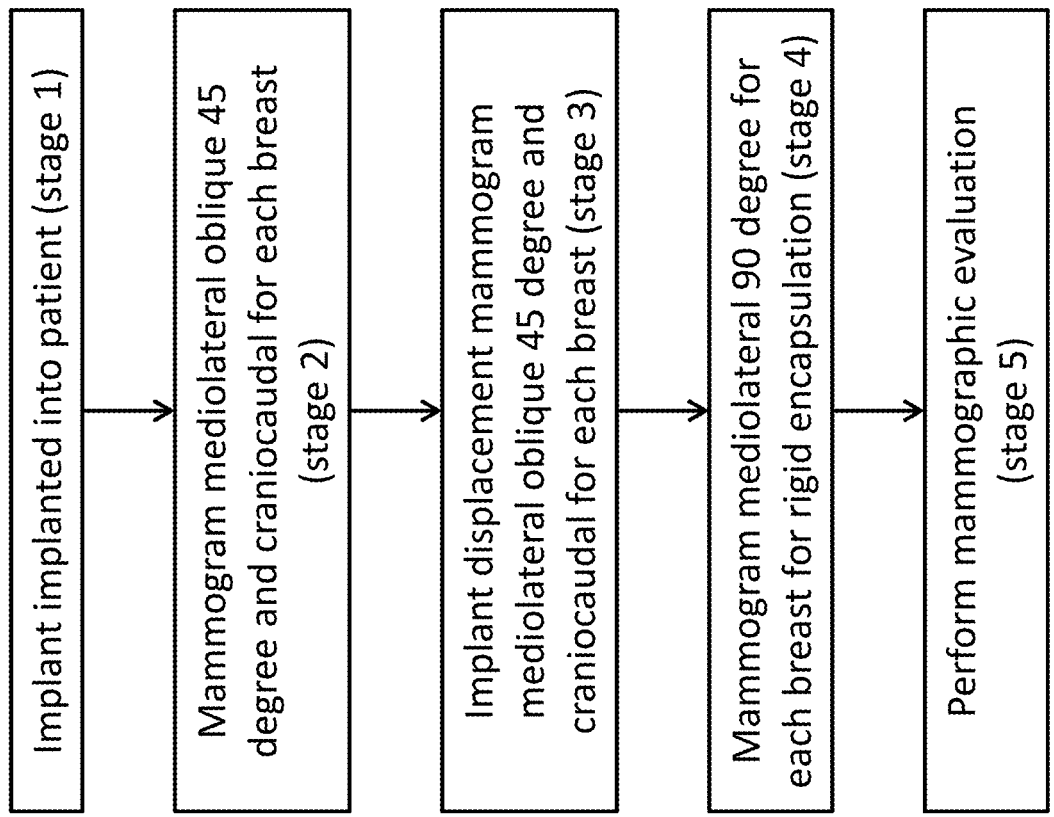
FIGS. 8A and 8B are flow diagrams of a prior art method for mammographic imaging and a method according to at least some embodiments of the present invention.
Figure 8B:
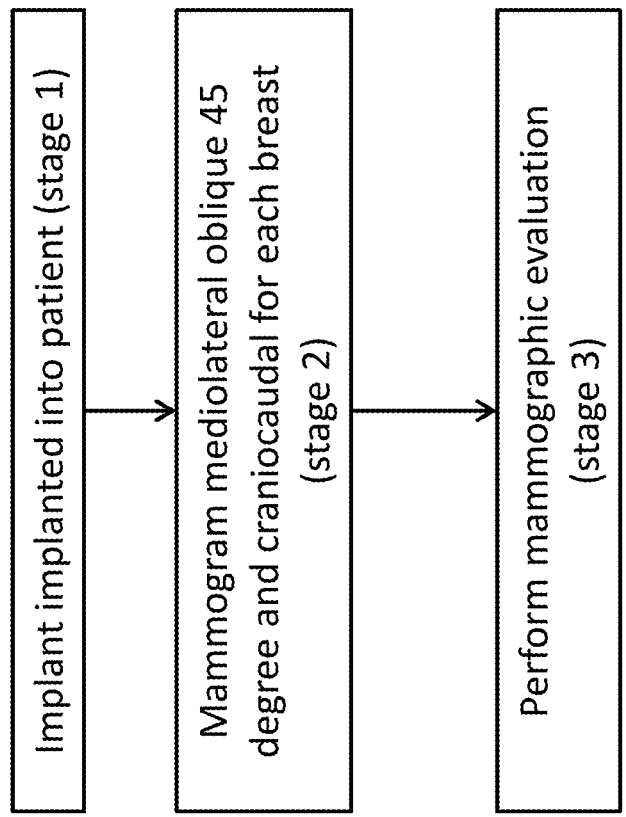

Reference is now made to FIG. 8B which is a flow diagram of the mammography process for a patient with an implant according to at least some embodiments of the present invention. As shown in stage 1 the patient undergoes surgery to implant the implant which is the implant of the present invention comprising additives as described in any of the embodiments described above.

In stage 2 the patient undergoes a routine screening mammography comprising mediolateral oblique 45 degree imaging and craniocaudal imaging for each breast. Optionally any standard imaging for a screening mammography is performed as required by local medical standards. Optionally, as in FIG. 8B, implant displacement or any other techniques for moving the implant for the purposes of imaging are not required. The imaging is performed with the implant in position and in stage 3 evaluation of the mammography images is performed by a medical professional for determination of the presence of anomalies where the implant does not obscure underlying tissue in the image.

While the invention has been described with respect to a limited number of embodiments, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A prosthetic implant, suitable for implantation to the human body, comprising a composite material comprising a base material selected from a polymer network with a free molecule that may be a solvent or a free polymer chain; and a plurality of additives, wherein:
   a) said additives are selected from radiolucent additives and/or hyperechoic additives;
   b) said additives are selected such that the elastic modulus at 1 Hz of said composite material is greater than the elastic modulus of said base material, and wherein the elastic modulus of said composite material is greater than the elastic modulus of said base material by at least 20%;
   c) said additives have a surface roughness of between 0.2 nm and 40 nm Rids; and
   d) said additives are up to 500 microns in size with at least 20% size difference between them.

2. The implant of claim 1, wherein said additives comprise at least one of glass, ceramic, metal, polymers, PMMA, polyacrylonitrile, polybutadiene, PEEK, natural rubber, synthetic rubber, amorphous polymer or semi-crystalline polymer.

3. The implant of claim 1, wherein said base material comprises a silicone gel.

4. The implant of claim 1, comprising a plurality of shells, including at least one inner shell and at least one outer shell; wherein said at least one inner shell is at least partially surrounded by said outer shell; wherein said outer shell is filled with said base material and a plurality of hyperechoic additives, and wherein said inner shell is filled with said base material and a plurality of radiolucent additives.

5. The prosthetic implant of claim 1, wherein said additives are further selected such that the solvent concentration of said composite material is between 5%-95% of the solvent concentration of said base material.

6. The implant of claim 5, comprising a plurality of shells, including at least one inner shell and at least one outer shell; wherein said at least one inner shell is at least partially surrounded by said outer shell; wherein said outer shell is filled with said base material and a higher concentration of additives closer to said outer shell, and wherein said inner shell is filled with said base material and an increasing concentration of additives relative to the distance from said inner shell.

7. The implant of claim 1, wherein the elastic modulus is between 100% and 1000% greater.

8. The implant of claim 1, wherein the elastic modulus is between 100% and 500% greater.

9. The implant of claim 1, wherein said additives comprise a material selected from the group consisting of: Ethylene-acrylate rubber, Polyester Urethane, Bromo Isobutylene Isoprene, polybutadiene, epichlorohydrin, ethylene propylene, ethylene propylene diene monomer, polyether urethane, perfluorocarbon rubber, fluoronated hydrocarbon, fluoro silicone, fluorocarbon rubber, hydrogenated nitrile butadiene, polyisoprene, isobutylene isoprene butyl, acrylonitrile, butadiene, polyurethane, styrene butadiene, styrene ethylene butylene styrene copolymer, polysiloxane, vinyl methyl silicone, acrylonitrile butadiene carboxy monomer, styrene butadiene carboxy monomer, thermoplastic polyether-ester, Styrene butadiene block copolymer, and styrene butadiene carboxy block copolymer.

10. The implant of claim 2, wherein said additives have at least one of the following characteristics: a) additives comprising a three-dimensional shape comprising spherical, fibrous, platelet, flakes, amorphous, crystalline, semi-sphere, rod, disk or combinations of these shapes or irregular versions of these shapes; b) hollow additives; c) porous additives; d) solid additives; e) additives comprising at least 2 materials; f) additives comprising a gas; g) additives comprising a non-solvent liquid; h) additives comprising a non-silicone gel; i) additives formed as a micro-lumen; and j) a combination of the above.

11. A composite material suitable for implantation to the human body, comprising a base material; and a plurality of additives, wherein:
   a) said additives are selected from radiolucent additives and/or hyperechoic additives and/or hypoechoic additives;
   b) said additives are selected such that the elastic modulus at 1 Hz of said composite material is greater than the elastic modulus of said base material, and wherein the elastic modulus is greater than the elastic modulus of said base material by at least 20%;
   c) said additives have a surface roughness of between 0.2 nm and 40 nm $R_{RMS}$; and
   d) said additives are up to 500 microns in size with at least 20% size difference between them.

12. The material of claim 11, wherein said additives comprise up to 60% by volume of the composite material.

13. The material of claim 11, wherein said additives comprise up to 90% by volume of the composite material.

14. The material of claim 11, wherein said base material is silicone gel.

15. The composite material of claim 11, wherein said additives are further selected such that the solvent concentration of said composite material is 5%-95% of the solvent concentration of said base material.

16. The composite material of claim 11, wherein said additives are further selected such that the elastic modulus at 1 Hz of said composite material is 20%-5000% greater than the elastic modulus of said base material.

17. The composite material of claim 11, wherein the base material comprises a polymer network with a free molecule that may be a solvent or a free polymer chain.

18. A method for performing a screening mammography of a breast comprising an implant according to claim 1, the method comprising: a) performing a mammography on one or both breasts; and b) evaluating the mammographic images; wherein implant displacement is not performed during said performing of said mammography, wherein said implant comprises a composite material comprising a base material and a plurality of additives, wherein said additives are selected from radiolucent additives.

19. A method for performing a mammography of a breast comprising an implant according to claim 1, the method comprising: performing a mammography on one or both breasts; wherein the resulting mammographic image comprises said implant and wherein said implant comprises a composite material comprising a base material and a plurality of additives, wherein said additives are selected from radiolucent additives such that said implant does not completely obscure breast tissue in said image.

20. A method for detection in a patient of extravasated implant material that has escaped from a ruptured implant, the method comprising: implanting an implant according to claim 1, comprising a composite material comprising a base material and a plurality of additives, wherein said additives are selected from hyperechoic or hypoechoic additives; performing ultrasonography on said patient; and detecting said extravasated material by its hyperechoic or hypoechoic response.

21. A method for diagnosis of cancerous tissue in a breast comprising an implant according to claim 1, the method comprising: a) implanting a prosthetic implant, suitable for implantation to the human body, comprising a composite material comprising a base material and a plurality of additives, wherein said additives are selected from radiolucent additives and/or hyperechoic additives; b) capturing a diagnostic radiology image of the breast wherein said image comprises said prosthetic implant; and c) determining the presence of calcifications in breast tissue visible on said image behind or in front of said implant.

* * * * *